(12) United States Patent
Lawes et al.

(10) Patent No.: US 8,257,352 B2
(45) Date of Patent: Sep. 4, 2012

(54) BIPOLAR FORCEPS HAVING MONOPOLAR EXTENSION

(75) Inventors: Kate Lawes, Austin, TX (US); Sean T. Dycus, Broomfield, CO (US); Ned Cosgriff, Denver, CO (US)

(73) Assignee: Covidien AG (CH)

( * ) Notice: Subject to any disclaimer, the term of this patent is extended or adjusted under 35 U.S.C. 154(b) by 0 days.

(21) Appl. No.: 12/876,662

(22) Filed: Sep. 7, 2010

(65) Prior Publication Data

US 2011/0004209 A1    Jan. 6, 2011

Related U.S. Application Data

(62) Division of application No. 11/904,123, filed on Sep. 26, 2007, now abandoned, which is a division of application No. 10/988,950, filed on Nov. 15, 2004, now Pat. No. 7,367,976.

(60) Provisional application No. 60/520,579, filed on Nov. 17, 2003.

(51) Int. Cl.
*A61B 18/18* (2006.01)

(52) U.S. Cl. ........... 606/51; 606/41; 606/48; 606/50; 606/52

(58) Field of Classification Search ........... 606/1, 45, 606/50–52, 37, 39–42
See application file for complete search history.

(56) References Cited

U.S. PATENT DOCUMENTS

| | | | |
|---|---|---|---|
| 371,664 A | 10/1887 | Brannan et al. | |
| 702,472 A | 6/1902 | Pignolet | |
| 728,883 A | 5/1903 | Downes | |
| 1,586,645 A | 6/1926 | Bierman | |
| 1,813,902 A | 7/1931 | Bovie | |
| 1,822,330 A | 9/1931 | Ainslie | |
| 1,852,542 A | 4/1932 | Sovatkin | |
| 1,908,201 A | 5/1933 | Welch et al. | |
| 1,918,889 A | 7/1933 | Bacon | |
| 2,002,594 A | 5/1935 | Wappler et al. | |

(Continued)

FOREIGN PATENT DOCUMENTS

CA    2 104 423    2/1994

(Continued)

OTHER PUBLICATIONS

U.S. Appl. No. 09/387,883, filed Sep. 1, 1999.

(Continued)

*Primary Examiner* — Linda Dvorak
*Assistant Examiner* — Jaymi Della

(57) ABSTRACT

An endoscopic forceps for treating tissue includes a housing having a shaft affixed thereto which has first and second jaw members attached to a distal end thereof. The forceps also includes an actuator for moving jaw members relative to one another from a first position wherein the jaw members are disposed in spaced relation relative to one another to a second position wherein the jaw members cooperate to grasp tissue therebetween. Each of the jaw members is connected to a source of electrosurgical energy such that the jaw members are selectively capable of operating in a bipolar mode which enables the jaw members to conduct bipolar energy through tissue held therebetween to treat tissue. The forceps also includes a monopolar element housed within the first jaw member which is selectively movable from a first position within the first jaw member to a second position distal to the first jaw member. The monopolar element is connected to the source of electrosurgical energy and is selectively activateable independent of the bipolar mode.

6 Claims, 8 Drawing Sheets

U.S. PATENT DOCUMENTS

| | | |
|---|---|---|
| 2,011,169 A | 8/1935 | Wappler |
| 2,031,682 A | 2/1936 | Wappler et al. |
| 2,054,149 A | 9/1936 | Wappler |
| 2,113,246 A | 5/1937 | Wappler |
| 2,176,479 A | 10/1939 | Willis |
| 2,305,156 A | 4/1941 | Grubel |
| 2,279,753 A | 4/1942 | Knopp |
| 2,327,353 A | 8/1943 | Karle |
| 2,632,661 A | 8/1948 | Cristofv |
| 2,668,538 A | 2/1954 | Baker |
| 2,796,065 A | 6/1957 | Kapp |
| 3,073,311 A | 1/1963 | Tibbs et al. |
| 3,100,489 A | 8/1963 | Bagley |
| 3,372,288 A | 3/1968 | Wigington |
| 3,459,187 A | 8/1969 | Pallotta |
| 3,561,448 A | 2/1971 | Peternel |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,875,945 A | 4/1975 | Friedman |
| 3,897,786 A | 8/1975 | Garnett et al. |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| D249,549 S | 9/1978 | Pike |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,200,104 A | 4/1980 | Harris |
| 4,233,734 A | 11/1980 | Bies |
| 4,236,470 A | 12/1980 | Stenson |
| 4,274,413 A | 6/1981 | Hahn et al. |
| 4,300,564 A | 11/1981 | Furihata |
| 4,306,561 A | 12/1981 | De Medinaceli |
| 4,311,145 A | 1/1982 | Esty et al. |
| D263,020 S | 2/1982 | Rau, III |
| 4,315,510 A | 2/1982 | Kihn |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,513,271 A | 4/1985 | Reisem |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,619,258 A | 10/1986 | Pool |
| 4,624,254 A | 11/1986 | McGarry et al. |
| 4,644,950 A | 2/1987 | Valli |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,674,499 A | 6/1987 | Pao |
| 4,685,459 A | 8/1987 | Xoch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| D298,353 S | 11/1988 | Manno |
| D299,413 S | 1/1989 | DeCarolis |
| 4,805,616 A | 2/1989 | Pao |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,890,610 A | 1/1990 | Kirwan, Sr. et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,122,139 A | 6/1992 | Sutter |
| 5,147,357 A | 9/1992 | Rose et al. |
| 5,151,102 A | 9/1992 | Kamiyama et al. |
| 5,151,978 A | 9/1992 | Bronikowski et al. |
| 5,158,561 A | 10/1992 | Rydell et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,267,998 A | 12/1993 | Hagen |
| 5,269,780 A | 12/1993 | Roos |
| 5,269,804 A | 12/1993 | Bales et al. |
| D343,453 S | 1/1994 | Noda |
| 5,275,615 A | 1/1994 | Rose |
| 5,277,201 A | 1/1994 | Stern |
| 5,281,220 A | 1/1994 | Blake, III |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,313,027 A | 5/1994 | Inoue et al. |
| 5,314,445 A | 5/1994 | Degwitz et al. |
| 5,318,589 A | 6/1994 | Lichtman |

| | | | | | |
|---|---|---|---|---|---|
| 5,324,289 A | 6/1994 | Eggers | 5,482,054 A | 1/1996 | Slater et al. |
| D348,930 S | 7/1994 | Olson | 5,484,436 A | 1/1996 | Eggers et al. |
| 5,326,806 A | 7/1994 | Yokoshima et al. | 5,493,899 A | 2/1996 | Beck et al. |
| 5,330,471 A | 7/1994 | Eggers | 5,496,312 A | 3/1996 | Klicek |
| 5,330,502 A | 7/1994 | Hassler et al. | 5,496,317 A | 3/1996 | Goble et al. |
| D349,341 S | 8/1994 | Lichtman et al. | 5,496,347 A | 3/1996 | Hashiguchi et al. |
| 5,334,183 A | 8/1994 | Wuchinich | 5,499,997 A | 3/1996 | Sharpe et al. |
| 5,334,215 A | 8/1994 | Chen | 5,509,922 A | 4/1996 | Aranyi et al. |
| 5,336,220 A | 8/1994 | Ryan et al. | 5,512,721 A | 4/1996 | Young et al. |
| 5,336,221 A | 8/1994 | Anderson | 5,514,134 A | 5/1996 | Rydell et al. |
| 5,342,359 A | 8/1994 | Rydell | 5,520,702 A | 5/1996 | Sauer et al. |
| 5,342,381 A | 8/1994 | Tidemand | 5,527,313 A | 6/1996 | Scott et al. |
| 5,342,393 A | 8/1994 | Stack | 5,528,833 A | 6/1996 | Sakuma |
| 5,344,424 A | 9/1994 | Roberts et al. | 5,529,067 A | 6/1996 | Larsen et al. |
| 5,350,391 A | 9/1994 | Iacovelli | 5,531,744 A | 7/1996 | Nardella et al. |
| 5,352,222 A | 10/1994 | Rydell | 5,536,251 A | 7/1996 | Evard et al. |
| 5,354,271 A | 10/1994 | Voda | 5,540,684 A | 7/1996 | Hassler, Jr. |
| 5,356,408 A | 10/1994 | Rydell | 5,540,685 A | 7/1996 | Parins et al. |
| 5,359,993 A | 11/1994 | Slater et al. | 5,540,706 A | 7/1996 | Aust et al. |
| 5,366,477 A | 11/1994 | LeMarie, III et al. | 5,540,715 A | 7/1996 | Katsaros et al. |
| 5,367,250 A | 11/1994 | Whisenand | 5,542,945 A | 8/1996 | Fritzsch |
| 5,368,600 A | 11/1994 | Failla et al. | 5,549,604 A | 8/1996 | Sutcu et al. |
| 5,374,277 A | 12/1994 | Hassler | 5,558,671 A | 9/1996 | Yates |
| 5,376,089 A | 12/1994 | Smith | 5,558,672 A | 9/1996 | Edwards et al. |
| 5,376,094 A | 12/1994 | Kline | 5,562,619 A | 10/1996 | Mirarchi et al. |
| D354,564 S | 1/1995 | Medema | 5,562,699 A | 10/1996 | Heimberger et al. |
| 5,383,875 A | 1/1995 | Bays et al. | 5,562,720 A | 10/1996 | Stern et al. |
| 5,383,880 A | 1/1995 | Hooven | 5,564,615 A | 10/1996 | Bishop et al. |
| 5,383,897 A | 1/1995 | Wholey | 5,569,241 A | 10/1996 | Edwardds |
| 5,389,098 A | 2/1995 | Tsuruta et al. | 5,569,243 A | 10/1996 | Kortenbach et al. |
| 5,389,103 A | 2/1995 | Melzer et al. | 5,571,100 A | 11/1996 | Goble et al. |
| 5,389,104 A | 2/1995 | Hahnen et al. | 5,573,424 A | 11/1996 | Poppe |
| 5,391,166 A | 2/1995 | Eggers | 5,573,534 A | 11/1996 | Stone |
| 5,391,183 A | 2/1995 | Janzen et al. | 5,573,535 A | 11/1996 | Viklund |
| 5,395,360 A | 3/1995 | Manoukian | 5,575,799 A | 11/1996 | Bolanos et al. |
| 5,396,900 A | 3/1995 | Slater et al. | 5,575,805 A | 11/1996 | Li |
| 5,403,312 A | 4/1995 | Yates et al. | 5,578,052 A | 11/1996 | Koros et al. |
| 5,403,342 A | 4/1995 | Tovey et al. | 5,579,781 A | 12/1996 | Cooke |
| 5,405,344 A | 4/1995 | Williamson et al. | 5,582,611 A | 12/1996 | Tsukagoshi et al. |
| 5,409,763 A | 4/1995 | Serizawa et al. | 5,582,617 A | 12/1996 | Klieman et al. |
| D358,887 S | 5/1995 | Feinberg | 5,585,896 A | 12/1996 | Yamazaki et al. |
| 5,411,519 A | 5/1995 | Tovey et al. | 5,590,570 A | 1/1997 | LeMaire, III et al. |
| 5,411,520 A | 5/1995 | Nash et al. | 5,591,181 A | 1/1997 | Stone et al. |
| 5,413,571 A | 5/1995 | Katsaros et al. | 5,597,107 A | 1/1997 | Knodel et al. |
| 5,415,656 A | 5/1995 | Tihon et al. | 5,599,350 A | 2/1997 | Schulze et al. |
| 5,415,657 A | 5/1995 | Taymor-Luria | 5,601,224 A | 2/1997 | Bishop et al. |
| 5,417,709 A | 5/1995 | Slater | 5,601,601 A | 2/1997 | Tal et al. |
| 5,422,567 A | 6/1995 | Matsunaga | 5,601,641 A | 2/1997 | Stephens |
| 5,423,810 A | 6/1995 | Goble et al. | 5,603,711 A | 2/1997 | Parins et al. |
| 5,425,690 A | 6/1995 | Chang | 5,603,723 A | 2/1997 | Aranyi et al. |
| 5,425,739 A | 6/1995 | Jessen | 5,607,436 A | 3/1997 | Pratt et al. |
| 5,429,616 A | 7/1995 | Schaffer | 5,611,798 A | 3/1997 | Eggers |
| 5,431,672 A | 7/1995 | Cote et al. | 5,611,808 A | 3/1997 | Hossain et al. |
| 5,431,674 A | 7/1995 | Basile et al. | 5,611,813 A | 3/1997 | Lichtman |
| 5,437,292 A | 8/1995 | Kipshidze et al. | 5,618,307 A | 4/1997 | Donlon et al. |
| 5,438,302 A | 8/1995 | Goble | 5,620,415 A | 4/1997 | Lucey et al. |
| 5,439,478 A | 8/1995 | Palmer | 5,620,453 A | 4/1997 | Nallakrishnan |
| 5,441,517 A | 8/1995 | Kensey et al. | 5,620,459 A | 4/1997 | Lichtman |
| 5,443,463 A | 8/1995 | Stern et al. | 5,624,452 A | 4/1997 | Yates |
| 5,443,464 A | 8/1995 | Russell et al. | 5,626,578 A | 5/1997 | Tihon |
| 5,443,480 A | 8/1995 | Jacobs et al. | 5,626,607 A | 5/1997 | Malecki et al. |
| 5,445,638 A | 8/1995 | Rydell et al. | 5,626,609 A | 5/1997 | Zvenyatsky et al. |
| 5,445,658 A | 8/1995 | Durrfeld et al. | 5,630,833 A | 5/1997 | Katsaros et al. |
| 5,449,480 A | 9/1995 | Kuriya et al. | 5,637,110 A | 6/1997 | Pennybacker et al. |
| 5,451,224 A | 9/1995 | Goble et al. | 5,638,003 A | 6/1997 | Hall |
| 5,454,809 A | 10/1995 | Janssen | 5,639,403 A | 6/1997 | Ida et al. |
| 5,454,823 A | 10/1995 | Richardson et al. | 5,643,294 A | 7/1997 | Tovey et al. |
| 5,454,827 A | 10/1995 | Aust et al. | 5,647,869 A | 7/1997 | Goble et al. |
| 5,456,684 A | 10/1995 | Schmidt et al. | 5,647,871 A | 7/1997 | Levine et al. |
| 5,458,598 A | 10/1995 | Feinberg et al. | 5,649,959 A | 7/1997 | Hannam et al. |
| 5,460,629 A | 10/1995 | Shlain et al. | 5,655,650 A | 8/1997 | Naitou |
| 5,461,765 A | 10/1995 | Linden et al. | 5,658,281 A | 8/1997 | Heard |
| 5,462,546 A | 10/1995 | Rydell | D384,413 S | 9/1997 | Zlock et al. |
| 5,472,442 A | 12/1995 | Klicek | 5,662,667 A | 9/1997 | Knodel |
| 5,472,443 A | 12/1995 | Cordis et al. | 5,665,100 A | 9/1997 | Yoon |
| 5,476,479 A | 12/1995 | Green et al. | 5,667,526 A | 9/1997 | Levin |
| 5,478,351 A | 12/1995 | Meade et al. | 5,674,220 A | 10/1997 | Fox et al. |
| 5,480,406 A | 1/1996 | Nolan et al. | 5,674,229 A | 10/1997 | Tovey et al. |
| 5,480,409 A | 1/1996 | Riza | 5,681,282 A | 10/1997 | Eggers et al. |

| | | | | | | |
|---|---|---|---|---|---|---|
| 5,688,270 A | 11/1997 | Yates et al. | | 5,876,412 A | 3/1999 | Piraka |
| 5,690,652 A | 11/1997 | Wurster et al. | | 5,882,567 A | 3/1999 | Cavallaro et al. |
| 5,690,653 A | 11/1997 | Richardson et al. | | 5,891,141 A | 4/1999 | Rydell |
| 5,693,051 A | 12/1997 | Schulze et al. | | 5,891,142 A | 4/1999 | Eggers et al. |
| 5,693,920 A | 12/1997 | Maeda | | 5,893,863 A | 4/1999 | Yoon |
| 5,695,522 A | 12/1997 | LeMaire, III et al. | | 5,893,875 A | 4/1999 | O'Connor et al. |
| 5,700,261 A | 12/1997 | Brinkerhoff | | 5,893,877 A | 4/1999 | Gampp, Jr. et al. |
| 5,700,270 A | 12/1997 | Peyser et al. | | 5,897,563 A | 4/1999 | Yoon et al. |
| 5,702,390 A | 12/1997 | Austin et al. | | 5,902,301 A | 5/1999 | Olig |
| 5,707,369 A | 1/1998 | Vaitekunas et al. | | 5,906,630 A | 5/1999 | Anderhub et al. |
| 5,709,680 A | 1/1998 | Yates et al. | | 5,908,420 A | 6/1999 | Parins et al. |
| 5,716,366 A | 2/1998 | Yates | | 5,908,432 A | 6/1999 | Pan |
| 5,720,742 A | 2/1998 | Zacharias | | 5,911,719 A | 6/1999 | Eggers |
| 5,720,744 A | 2/1998 | Eggleston et al. | | 5,913,874 A | 6/1999 | Berns et al. |
| 5,722,421 A | 3/1998 | Francese et al. | | 5,921,916 A | 7/1999 | Aeikens et al. |
| 5,725,536 A | 3/1998 | Oberlin et al. | | 5,921,984 A | 7/1999 | Sutcu et al. |
| 5,727,428 A | 3/1998 | LeMaire, III et al. | | 5,925,043 A | 7/1999 | Kumar et al. |
| 5,735,848 A | 4/1998 | Yates et al. | | 5,928,136 A | 7/1999 | Barry |
| 5,743,906 A | 4/1998 | Parins et al. | | 5,935,126 A | 8/1999 | Riza |
| 5,752,973 A | 5/1998 | Kieturakis | | 5,938,589 A | 8/1999 | Wako et al. |
| 5,755,717 A | 5/1998 | Yates et al. | | 5,941,869 A | 8/1999 | Patterson et al. |
| 5,759,188 A | 6/1998 | Yoon | | 5,944,718 A | 8/1999 | Dafforn et al. |
| 5,762,255 A | 6/1998 | Chrisman et al. | | 5,951,545 A | 9/1999 | Schilling et al. |
| 5,762,609 A | 6/1998 | Benaron et al. | | 5,951,546 A | 9/1999 | Lorentzen |
| 5,766,130 A | 6/1998 | Selmonosky | | 5,951,549 A | 9/1999 | Richardson et al. |
| 5,766,166 A | 6/1998 | Hooven | | 5,954,720 A | 9/1999 | Wilson et al. |
| 5,766,170 A | 6/1998 | Eggers | | 5,954,731 A | 9/1999 | Yoon |
| 5,766,196 A | 6/1998 | Griffiths | | 5,954,733 A | 9/1999 | Yoon |
| 5,769,849 A | 6/1998 | Eggers | | 5,957,923 A | 9/1999 | Hahnen et al. |
| 5,772,655 A | 6/1998 | Bauer et al. | | 5,957,937 A | 9/1999 | Yoon |
| 5,772,670 A | 6/1998 | Brosa | | 5,960,544 A | 10/1999 | Beyers |
| 5,776,128 A | 7/1998 | Eggers | | 5,961,514 A | 10/1999 | Long et al. |
| 5,776,130 A | 7/1998 | Buysse et al. | | 5,964,758 A | 10/1999 | Dresden |
| 5,776,156 A | 7/1998 | Shikhman | | D416,089 S | 11/1999 | Barton et al. |
| 5,779,646 A | 7/1998 | Koblish et al. | | 5,976,132 A | 11/1999 | Morris |
| 5,779,701 A | 7/1998 | McBrayer et al. | | 5,984,932 A | 11/1999 | Yoon |
| 5,779,727 A | 7/1998 | Orejola | | 5,984,938 A | 11/1999 | Yoon |
| H1745 H | 8/1998 | Paraschac | | 5,984,939 A | 11/1999 | Yoon |
| 5,792,137 A | 8/1998 | Carr et al. | | 5,989,277 A | 11/1999 | LeMaire, III et al. |
| 5,792,165 A | 8/1998 | Klieman et al. | | 5,993,466 A | 11/1999 | Yoon |
| 5,792,177 A | 8/1998 | Kaseda | | 5,993,467 A | 11/1999 | Yoon |
| 5,797,537 A | 8/1998 | Oberlin et al. | | 5,997,565 A | 12/1999 | Inoue |
| 5,797,927 A | 8/1998 | Yoon | | 6,003,517 A * | 12/1999 | Sheffield et al. ............... 128/898 |
| 5,797,938 A | 8/1998 | Paraschac et al. | | 6,004,332 A | 12/1999 | Yoon et al. |
| 5,797,941 A | 8/1998 | Schulze et al. | | 6,004,335 A | 12/1999 | Vaitekunas et al. |
| 5,797,958 A | 8/1998 | Yoon | | 6,010,516 A | 1/2000 | Hulka et al. |
| 5,797,959 A | 8/1998 | Castro et al. | | 6,017,354 A | 1/2000 | Culp et al. |
| 5,800,448 A | 9/1998 | Banko | | 6,017,358 A | 1/2000 | Yoon et al. |
| 5,800,449 A | 9/1998 | Wales | | 6,021,693 A | 2/2000 | Feng-Sing |
| 5,807,393 A | 9/1998 | Williamsom, IV et al. | | 6,024,741 A | 2/2000 | Williamson et al. |
| 5,810,764 A | 9/1998 | Eggers et al. | | 6,024,743 A | 2/2000 | Edwards |
| 5,810,805 A | 9/1998 | Sutcu et al. | | 6,024,744 A | 2/2000 | Kese et al. |
| 5,810,808 A | 9/1998 | Eggers | | 6,027,522 A | 2/2000 | Palmer |
| 5,810,811 A | 9/1998 | Yates et al. | | 6,030,384 A | 2/2000 | Nezhat |
| 5,810,877 A | 9/1998 | Roth et al. | | 6,033,399 A | 3/2000 | Gines |
| 5,814,043 A | 9/1998 | Shapeton | | 6,039,733 A | 3/2000 | Buysse et al. |
| 5,814,054 A | 9/1998 | Kortenbach et al. | | 6,041,679 A | 3/2000 | Slater et al. |
| 5,817,093 A | 10/1998 | Williamson, IV et al. | | 6,050,996 A | 4/2000 | Schmaltz et al. |
| 5,817,119 A | 10/1998 | Klieman et al. | | 6,053,914 A | 4/2000 | Eggers et al. |
| 5,820,630 A | 10/1998 | Lind | | 6,053,933 A | 4/2000 | Balazs et al. |
| 5,824,978 A | 10/1998 | Karasik et al. | | D424,694 S | 5/2000 | Tetzlaff et al. |
| 5,827,271 A | 10/1998 | Buysse et al. | | D425,201 S | 5/2000 | Tetzlaff et al. |
| 5,827,279 A | 10/1998 | Hughett et al. | | 6,059,782 A | 5/2000 | Novak et al. |
| 5,827,281 A | 10/1998 | Levin | | 6,063,103 A | 5/2000 | Hashiguchi |
| 5,827,323 A | 10/1998 | Klieman et al. | | 6,066,139 A | 5/2000 | Ryan et al. |
| 5,827,548 A | 10/1998 | Lavallee et al. | | 6,071,283 A | 6/2000 | Nardella et al. |
| 5,830,212 A | 11/1998 | Cartmell et al. | | 6,074,386 A | 6/2000 | Goble et al. |
| 5,833,690 A | 11/1998 | Yates et al. | | 6,077,287 A | 6/2000 | Taylor et al. |
| 5,833,695 A | 11/1998 | Yoon | | 6,080,180 A | 6/2000 | Yoon et al. |
| D402,028 S | 12/1998 | Grimm et al. | | RE36,795 E | 7/2000 | Rydell |
| 5,843,080 A | 12/1998 | Fleenor et al. | | 6,083,223 A | 7/2000 | Baker |
| 5,849,022 A | 12/1998 | Sakashita et al. | | 6,086,586 A | 7/2000 | Hooven |
| 5,851,214 A | 12/1998 | Larsen et al. | | 6,086,601 A | 7/2000 | Yoon |
| 5,853,412 A | 12/1998 | Mayenberger | | 6,090,107 A | 7/2000 | Borgmeier et al. |
| 5,859,527 A | 1/1999 | Cook | | 6,090,123 A | 7/2000 | Culp et al. |
| 5,860,976 A | 1/1999 | Billings et al. | | 6,096,037 A | 8/2000 | Mulier et al. |
| 5,865,361 A | 2/1999 | Milliman et al. | | 6,099,550 A | 8/2000 | Yoon |
| 5,876,401 A | 3/1999 | Schulze et al. | | 6,102,909 A | 8/2000 | Chen et al. |
| 5,876,410 A | 3/1999 | Petillo | | 6,106,542 A | 8/2000 | Toybin et al. |

| | | |
|---|---|---|
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,122,549 A | 9/2000 | Sharkey et al. |
| 6,123,701 A | 9/2000 | Nezhat |
| H1904 H | 10/2000 | Yates et al. |
| 6,126,658 A | 10/2000 | Baker |
| 6,126,665 A | 10/2000 | Yoon |
| 6,139,563 A | 10/2000 | Cosgrove, III et al. |
| 6,143,005 A | 11/2000 | Yoon et al. |
| 6,152,923 A | 11/2000 | Ryan |
| 6,152,924 A | 11/2000 | Parins |
| 6,162,220 A | 12/2000 | Nezhat |
| 6,171,316 B1 | 1/2001 | Kovac et al. |
| 6,174,309 B1 | 1/2001 | Wrublewski et al. |
| 6,174,310 B1 | 1/2001 | Kirwan, Jr. |
| 6,178,628 B1 | 1/2001 | Clemens et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 * | 2/2001 | Rydell .................. 606/51 |
| 6,190,400 B1 | 2/2001 | Vandemoer et al. |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,206,893 B1 | 3/2001 | Klein et al. |
| 6,214,028 B1 | 4/2001 | Yoon et al. |
| 6,217,602 B1 | 4/2001 | Redmon |
| 6,217,615 B1 | 4/2001 | Sioshansi et al. |
| 6,221,039 B1 | 4/2001 | Durgin et al. |
| 6,223,100 B1 | 4/2001 | Green |
| 6,224,593 B1 | 5/2001 | Ryan et al. |
| 6,224,614 B1 | 5/2001 | Yoon |
| 6,228,080 B1 | 5/2001 | Gines |
| 6,228,083 B1 | 5/2001 | Lands et al. |
| 6,248,124 B1 | 6/2001 | Pedros et al. |
| 6,248,944 B1 | 6/2001 | Ito |
| 6,261,307 B1 | 7/2001 | Yoon et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,298,550 B1 | 10/2001 | Kirwan |
| 6,302,424 B1 | 10/2001 | Gisinger et al. |
| 6,309,404 B1 | 10/2001 | Krzyzanowski |
| 6,319,262 B1 | 11/2001 | Bates et al. |
| 6,319,451 B1 | 11/2001 | Brune |
| 6,322,561 B1 | 11/2001 | Eggers et al. |
| 6,322,580 B1 | 11/2001 | Kanner |
| 6,325,795 B1 | 12/2001 | Lindemann et al. |
| 6,329,778 B1 | 12/2001 | Culp et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| D454,951 S | 3/2002 | Bon |
| 6,352,536 B1 | 3/2002 | Buysse et al. |
| 6,358,249 B1 | 3/2002 | Chen et al. |
| 6,358,259 B1 | 3/2002 | Swain et al. |
| 6,358,268 B1 | 3/2002 | Hunt et al. |
| 6,361,534 B1 | 3/2002 | Chen et al. |
| 6,364,879 B1 | 4/2002 | Chen et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,129 B2 | 10/2002 | Scarfi |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,471,696 B1 | 10/2002 | Berube et al. |
| D465,281 S | 11/2002 | Lang |
| D466,209 S | 11/2002 | Bon |
| 6,485,489 B2 | 11/2002 | Teirstein et al. |
| 6,488,680 B1 | 12/2002 | Francischelli et al. |
| 6,494,888 B1 | 12/2002 | Laufer et al. |
| 6,500,176 B1 | 12/2002 | Truckai et al. |
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,252 B2 | 2/2003 | Nezhat et al. |
| 6,517,539 B1 | 2/2003 | Smith et al. |
| 6,527,771 B1 | 3/2003 | Weadock et al. |
| 6,533,784 B2 | 3/2003 | Truckai et al. |
| 6,545,239 B2 | 4/2003 | Spedale et al. |
| 6,558,385 B1 | 5/2003 | McClurken et al. |
| 6,562,037 B2 | 5/2003 | Paton et al. |
| 6,569,105 B1 | 5/2003 | Kortenbach et al. |
| 6,582,450 B2 | 6/2003 | Ouchi |
| 6,585,735 B1 | 7/2003 | Frazier et al. |
| 6,602,252 B2 | 8/2003 | Mollenauer |
| 6,605,790 B2 | 8/2003 | Yoshida |
| 6,616,654 B2 | 9/2003 | Mollenauer |
| 6,616,658 B2 | 9/2003 | Ineson |
| 6,616,661 B2 * | 9/2003 | Wellman et al. .................. 606/50 |
| 6,620,161 B2 | 9/2003 | Schulze et al. |
| 6,620,184 B2 | 9/2003 | De Laforcade et al. |
| 6,626,901 B1 | 9/2003 | Treat et al. |
| 6,638,287 B2 | 10/2003 | Danitz et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,173 B1 | 12/2003 | Palermo |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,663,639 B1 | 12/2003 | Laufer et al. |
| 6,663,641 B1 | 12/2003 | Kovac et al. |
| 6,666,854 B1 | 12/2003 | Lange |
| 6,669,696 B2 | 12/2003 | Bacher et al. |
| 6,673,092 B1 | 1/2004 | Bacher |
| 6,676,660 B2 | 1/2004 | Wampler et al. |
| 6,676,676 B2 | 1/2004 | Danitz et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,733,501 B2 | 5/2004 | Levine |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,338 B2 | 6/2004 | Hahnen et al. |
| 6,755,843 B2 | 6/2004 | Chung et al. |

| | | |
|---|---|---|
| 6,756,553 B1 | 6/2004 | Yamaguchi et al. |
| 6,757,977 B2 | 7/2004 | Dambal et al. |
| D493,888 S | 8/2004 | Reschke |
| 6,770,072 B1 | 8/2004 | Truckai et al. |
| 6,773,409 B2 | 8/2004 | Truckai et al. |
| 6,773,432 B1 | 8/2004 | Clayman et al. |
| 6,773,434 B2 | 8/2004 | Ciarrocca |
| 6,773,441 B1 | 8/2004 | Laufer et al. |
| 6,775,575 B2 | 8/2004 | Bommannan et al. |
| 6,776,780 B2 | 8/2004 | Mulier et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,818,007 B1 | 11/2004 | Dampney et al. |
| 6,821,285 B2 | 11/2004 | Laufer et al. |
| 6,830,174 B2 | 12/2004 | Hillstead et al. |
| 6,835,200 B2 | 12/2004 | Laufer et al. |
| 6,857,357 B2 | 2/2005 | Fujii |
| D502,994 S | 3/2005 | Blake, III |
| 6,860,880 B2 | 3/2005 | Treat et al. |
| 6,887,240 B1 | 5/2005 | Lands et al. |
| 6,889,116 B2 | 5/2005 | Jinno |
| 6,908,463 B2 | 6/2005 | Treat et al. |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| D509,297 S | 9/2005 | Wells |
| 6,942,662 B2 | 9/2005 | Goble et al. |
| 6,943,311 B2 | 9/2005 | Miyako |
| 6,951,559 B1 | 10/2005 | Greep |
| 6,953,430 B2 | 10/2005 | Kodooka |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,972,017 B2 | 12/2005 | Smith et al. |
| 6,976,492 B2 | 12/2005 | Ingle et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |
| 6,994,707 B2 | 2/2006 | Ellman et al. |
| 6,994,709 B2 | 2/2006 | Iida |
| 6,997,931 B2 | 2/2006 | Sauer et al. |
| 7,001,381 B2 | 2/2006 | Harano et al. |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,489 B2 | 5/2006 | Griego et al. |
| 7,052,496 B2 | 5/2006 | Yamauchi |
| 7,063,715 B2 | 6/2006 | Onuki et al. |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,051 B2 | 8/2006 | Bourne et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,107,124 B2 | 9/2006 | Green |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| 7,137,980 B2 | 11/2006 | Buysse et al. |
| D533,274 S | 12/2006 | Visconti et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| 7,153,314 B2 | 12/2006 | Laufer et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,166,106 B2 | 1/2007 | Bartel et al. |
| 7,169,145 B2 | 1/2007 | Isaacson et al. |
| 7,169,146 B2 | 1/2007 | Truckai et al. |
| 7,179,255 B2 | 2/2007 | Lettice et al. |
| 7,179,258 B2 | 2/2007 | Buysse et al. |
| D538,932 S | 3/2007 | Malik |
| 7,195,631 B2 | 3/2007 | Dumbauld |
| D541,418 S | 4/2007 | Schechter et al. |
| 7,204,835 B2 | 4/2007 | Latterell et al. |
| 7,207,990 B2 | 4/2007 | Lands et al. |
| D541,611 S | 5/2007 | Aglassinger |
| D541,938 S | 5/2007 | Kerr et al |
| 7,211,084 B2 | 5/2007 | Goble et al. |
| 7,223,264 B2 | 5/2007 | Daniel et al. |
| 7,223,265 B2 | 5/2007 | Keppel |
| D545,432 S | 6/2007 | Watanabe |
| 7,232,440 B2 | 6/2007 | Dumbauld et al. |
| D547,154 S | 7/2007 | Lee |
| 7,238,184 B2 | 7/2007 | Megerman et al. |
| 7,241,288 B2 | 7/2007 | Braun |
| 7,241,296 B2 | 7/2007 | Buysse et al. |
| 7,244,257 B2 | 7/2007 | Podjahsky et al. |
| 7,246,734 B2 | 7/2007 | Shelto, IV |
| 7,248,944 B2 | 7/2007 | Green |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,311,709 B2 | 12/2007 | Truckai et al. |
| 7,314,471 B2 | 1/2008 | Holman |
| 7,318,823 B2 | 1/2008 | Sharps et al. |
| 7,329,256 B2 | 2/2008 | Johnson et al. |
| 7,329,257 B2 | 2/2008 | Kanehira et al. |
| D564,662 S | 3/2008 | Moses et al. |
| 7,338,526 B2 | 3/2008 | Steinberg |
| 7,342,754 B2 | 3/2008 | Fitzgerald et al. |
| 7,344,268 B2 | 3/2008 | Jhigamian |
| 7,347,864 B2 | 3/2008 | Vargas |
| D567,943 S | 4/2008 | Moses et al. |
| 7,354,440 B2 | 4/2008 | Truckal et al. |
| 7,367,976 B2 | 5/2008 | Lawes et al. |
| 7,377,920 B2 | 5/2008 | Buysse et al. |
| 7,384,420 B2 | 6/2008 | Dycus et al. |
| 7,384,421 B2 | 6/2008 | Hushka |
| 7,396,265 B2 | 7/2008 | Darley et al. |
| 7,396,336 B2 | 7/2008 | Orszulak et al. |
| 7,396,356 B2 | 7/2008 | Mollenauer |
| D575,395 S | 8/2008 | Hushka |
| D575,401 S | 8/2008 | Hixson et al. |
| 7,425,835 B2 | 9/2008 | Eisele |
| 7,431,721 B2 | 10/2008 | Paton et al. |
| 7,435,249 B2 | 10/2008 | Buysse et al. |
| 7,442,193 B2 | 10/2008 | Shields et al. |
| 7,442,194 B2 | 10/2008 | Dumbauld et al. |

| | | | | | | |
|---|---|---|---|---|---|---|
| 7,445,621 | B2 | 11/2008 | Dumbauld et al. | 2003/0171747 A1 | 9/2003 | Kanehira et al. |
| D582,038 | S | 12/2008 | Swoyer et al. | 2003/0181910 A1 | 9/2003 | Dycus et al. |
| 7,458,972 | B2 | 12/2008 | Keppel | 2003/0216732 A1 | 11/2003 | Truckai et al. |
| 7,473,253 | B2 | 1/2009 | Dycus et al. | 2003/0229344 A1 | 12/2003 | Dycus et al. |
| 7,481,810 | B2 | 1/2009 | Dumbauld et al. | 2003/0236325 A1 | 12/2003 | Bonora |
| 7,487,780 | B2 | 2/2009 | Hooven | 2004/0030330 A1 | 2/2004 | Brassell et al. |
| 7,491,201 | B2 | 2/2009 | Shields et al. | 2004/0064151 A1 | 4/2004 | Mollenauer |
| 7,491,202 | B2 | 2/2009 | Odom et al. | 2004/0073238 A1 | 4/2004 | Makower |
| 7,500,975 | B2 | 3/2009 | Cunningham et al. | 2004/0073256 A1 | 4/2004 | Marchitto et al. |
| 7,503,474 | B2 | 3/2009 | Hillstead et al. | 2004/0115296 A1 | 6/2004 | Duffin |
| 7,510,556 | B2 | 3/2009 | Nguyen et al. | 2004/0199181 A1 | 10/2004 | Knodel et al. |
| 7,513,898 | B2 | 4/2009 | Johnson et al. | 2004/0210282 A1 | 10/2004 | Flock et al. |
| 7,517,351 | B2 | 4/2009 | Culp et al. | 2004/0224590 A1 | 11/2004 | Rawa et al. |
| 7,540,872 | B2 | 6/2009 | Schechter et al. | 2004/0236326 A1 | 11/2004 | Schulze et al. |
| 7,549,995 | B2 | 6/2009 | Schultz | 2004/0249374 A1 | 12/2004 | Tetzlaff et al. |
| 7,553,312 | B2 | 6/2009 | Tetzlaff et al. | 2004/0260281 A1 | 12/2004 | Baxter, III et al. |
| 7,582,087 | B2 | 9/2009 | Tetzlaff et al. | 2005/0004564 A1 | 1/2005 | Wham et al. |
| 7,588,565 | B2 | 9/2009 | Marchitto et al. | 2005/0004569 A1 | 1/2005 | Witt et al. |
| 7,594,916 | B2 | 9/2009 | Weinberg | 2005/0033278 A1 | 2/2005 | McClurken et al. |
| 7,597,693 | B2 | 10/2009 | Garrison | 2005/0059858 A1 | 3/2005 | Frith et al. |
| 7,621,910 | B2 | 11/2009 | Sugi | 2005/0059934 A1 | 3/2005 | Wenchell et al. |
| 7,628,791 | B2 | 12/2009 | Garrison et al. | 2005/0096645 A1 | 5/2005 | Wellman et al. |
| 7,628,792 | B2 | 12/2009 | Guerra | 2005/0101952 A1 | 5/2005 | Lands et al. |
| 7,637,409 | B2 | 12/2009 | Marczyk | 2005/0149017 A1 | 7/2005 | Dycus |
| 7,641,653 | B2 | 1/2010 | Dalla Betta et al. | 2005/0197659 A1 | 9/2005 | Bahney |
| 7,651,493 | B2 | 1/2010 | Arts et al. | 2005/0203504 A1 | 9/2005 | Wham et al. |
| 7,651,494 | B2 | 1/2010 | McClurken et al. | 2005/0283148 A1 | 12/2005 | Janssen et al. |
| 7,655,007 | B2 | 2/2010 | Baily | 2006/0052779 A1 | 3/2006 | Hammill |
| 7,668,597 | B2 | 2/2010 | Engmark et al. | 2006/0064086 A1 | 3/2006 | Odom |
| 7,678,111 | B2 | 3/2010 | Mulier et al. | 2006/0079891 A1 | 4/2006 | Arts et al. |
| 7,686,804 | B2 | 3/2010 | Johnson et al. | 2006/0079933 A1 | 4/2006 | Hushka et al. |
| 7,686,827 | B2 | 3/2010 | Hushka | 2006/0084973 A1 | 4/2006 | Hushka |
| 7,708,735 | B2 | 5/2010 | Chapman et al. | 2006/0116675 A1 | 6/2006 | McClurken et al. |
| 7,717,115 | B2 | 5/2010 | Barrett et al. | 2006/0167452 A1 | 7/2006 | Moses et al. |
| 7,717,904 | B2 | 5/2010 | Suzuki et al. | 2006/0173452 A1 | 8/2006 | Buysse et al. |
| 7,717,914 | B2 | 5/2010 | Kimura | 2006/0190035 A1 | 8/2006 | Hushka et al. |
| 7,717,915 | B2 | 5/2010 | Miyazawa | 2006/0217709 A1 | 9/2006 | Couture et al. |
| 7,722,607 | B2 | 5/2010 | Dumbauld et al. | 2006/0253126 A1 | 11/2006 | Bjerken et al. |
| D617,900 | S | 6/2010 | Kingsley et al. | 2006/0259036 A1 | 11/2006 | Tetzlaff et al. |
| D617,901 | S | 6/2010 | Unger et al. | 2006/0264922 A1 | 11/2006 | Sartor et al. |
| D617,902 | S | 6/2010 | Twomey et al. | 2006/0283093 A1 | 12/2006 | Petrovic et al. |
| D617,903 | S | 6/2010 | Unger et al. | 2006/0287641 A1 | 12/2006 | Perlin |
| D618,798 | S | 6/2010 | Olson et al. | 2007/0016182 A1 | 1/2007 | Lipson et al. |
| 7,731,717 | B2 | 6/2010 | Odom et al. | 2007/0043353 A1 | 2/2007 | Dycus et al. |
| 7,744,615 | B2 | 6/2010 | Couture | 2007/0060919 A1 | 3/2007 | Isaacson et al. |
| 7,749,217 | B2 | 7/2010 | Podhajsky | 2007/0062017 A1 | 3/2007 | Dycus et al. |
| 7,753,908 | B2 | 7/2010 | Swanson | 2007/0074807 A1 | 4/2007 | Guerra |
| 7,753,909 | B2 | 7/2010 | Chapman et al. | 2007/0088356 A1 | 4/2007 | Moses et al. |
| D621,503 | S | 8/2010 | Otten et al. | 2007/0106295 A1 | 5/2007 | Garrison et al. |
| 7,766,910 | B2 | 8/2010 | Hixson et al. | 2007/0118115 A1 | 5/2007 | Artale et al. |
| 7,771,425 | B2 | 8/2010 | Dycus et al. | 2007/0142834 A1 | 6/2007 | Dumbauld |
| 7,776,036 | B2 | 8/2010 | Schechter et al. | 2007/0173804 A1 | 7/2007 | Wham et al. |
| 7,776,037 | B2 | 8/2010 | Odom | 2007/0173811 A1 | 7/2007 | Couture et al. |
| 7,780,662 | B2 | 8/2010 | Bahney | 2007/0173813 A1 | 7/2007 | Odom |
| 7,789,878 | B2 | 9/2010 | Dumbauld et al. | 2007/0198011 A1 | 8/2007 | Sugita |
| 7,799,026 | B2 | 9/2010 | Schechter et al. | 2007/0213712 A1 | 9/2007 | Buysse et al. |
| 7,799,028 | B2 | 9/2010 | Schechter et al. | 2007/0255279 A1 | 11/2007 | Buysse et al. |
| 7,811,283 | B2 | 10/2010 | Moses et al. | 2007/0260235 A1 | 11/2007 | Podhajsky |
| 7,819,872 | B2 | 10/2010 | Johnson et al. | 2007/0260238 A1 | 11/2007 | Guerra |
| D627,462 | S | 11/2010 | Kingsley | 2007/0260242 A1 | 11/2007 | Dycus et al. |
| D628,289 | S | 11/2010 | Romero | 2007/0265616 A1 | 11/2007 | Couture et al. |
| D628,290 | S | 11/2010 | Romero | 2008/0004616 A1 | 1/2008 | Patrick |
| 7,828,798 | B2 | 11/2010 | Buysse et al. | 2008/0015575 A1 | 1/2008 | Odom et al. |
| 7,837,685 | B2 | 11/2010 | Weinberg et al. | 2008/0033428 A1 | 2/2008 | Artale et al. |
| 7,846,161 | B2 | 12/2010 | Dumbauld et al. | 2008/0039831 A1 | 2/2008 | Odom et al. |
| 7,857,812 | B2 | 12/2010 | Dycus et al. | 2008/0039835 A1 | 2/2008 | Johnson et al. |
| D630,324 | S | 1/2011 | Reschke | 2008/0045947 A1 | 2/2008 | Johnson et al. |
| 7,972,331 | B2 * | 7/2011 | Hafner ............ 606/45 | 2008/0058802 A1 | 3/2008 | Couture et al. |
| 2002/0107517 | A1 | 8/2002 | Witt et al. | 2008/0082100 A1 | 4/2008 | Orton et al. |
| 2002/0111624 | A1 | 8/2002 | Witt et al. | 2008/0091189 A1 | 4/2008 | Carlton |
| 2003/0014052 | A1 | 1/2003 | Buysse et al. | 2008/0125767 A1 | 5/2008 | Blaha |
| 2003/0014053 | A1 | 1/2003 | Nguyen et al. | 2008/0125797 A1 | 5/2008 | Kelleher |
| 2003/0018332 | A1 | 1/2003 | Schmaltz et al. | 2008/0195093 A1 | 8/2008 | Couture et al. |
| 2003/0069570 | A1 | 4/2003 | Witzel et al. | 2008/0208289 A1 | 8/2008 | Darley et al. |
| 2003/0109875 | A1 | 6/2003 | Tetzlaff et al. | 2008/0215050 A1 | 9/2008 | Bakos |
| 2003/0114851 | A1 | 6/2003 | Truckai et al. | 2008/0234701 A1 | 9/2008 | Morales et al. |
| 2003/0130653 | A1 | 7/2003 | Sixto, Jr. et al. | 2008/0243120 A1 | 10/2008 | Lawes et al. |
| 2003/0139741 | A1 | 7/2003 | Goble et al. | 2008/0249527 A1 | 10/2008 | Couture |
| 2003/0158548 | A1 | 8/2003 | Phan et al. | 2008/0294222 A1 | 11/2008 | Schechter |

| | | |
|---|---|---|
| 2008/0296347 A1 | 12/2008 | Shelton, IV et al. |
| 2008/0300613 A1 | 12/2008 | Shelton, IV et al. |
| 2008/0312653 A1 | 12/2008 | Arts et al. |
| 2008/0319442 A1 | 12/2008 | Unger et al. |
| 2009/0012520 A1 | 1/2009 | Hixson et al. |
| 2009/0015832 A1 | 1/2009 | Popovic et al. |
| 2009/0024126 A1 | 1/2009 | Artale et al. |
| 2009/0036881 A1 | 2/2009 | Artale et al. |
| 2009/0036899 A1 | 2/2009 | Carlton et al. |
| 2009/0043304 A1 | 2/2009 | Tetzlaff et al. |
| 2009/0048596 A1 | 2/2009 | Shields et al. |
| 2009/0062794 A1 | 3/2009 | Buysse et al. |
| 2009/0065565 A1 | 3/2009 | Cao |
| 2009/0076534 A1 | 3/2009 | Shelton, IV et al. |
| 2009/0082766 A1 | 3/2009 | Unger et al. |
| 2009/0082767 A1 | 3/2009 | Unger et al. |
| 2009/0082769 A1 | 3/2009 | Unger et al. |
| 2009/0088738 A1 | 4/2009 | Guerra et al. |
| 2009/0088739 A1 | 4/2009 | Hushka et al. |
| 2009/0088740 A1 | 4/2009 | Guerra et al. |
| 2009/0088741 A1 | 4/2009 | Hushka et al. |
| 2009/0088744 A1 | 4/2009 | Townsend |
| 2009/0088745 A1 | 4/2009 | Hushka et al. |
| 2009/0088746 A1 | 4/2009 | Hushka et al. |
| 2009/0088747 A1 | 4/2009 | Hushka et al. |
| 2009/0088748 A1 | 4/2009 | Guerra et al. |
| 2009/0088749 A1 | 4/2009 | Hushka et al. |
| 2009/0088750 A1 | 4/2009 | Hushka et al. |
| 2009/0105750 A1 | 4/2009 | Price et al. |
| 2009/0112206 A1 | 4/2009 | Dumbauld et al. |
| 2009/0131934 A1 | 5/2009 | Odom et al. |
| 2009/0149853 A1 | 6/2009 | Shields et al. |
| 2009/0149854 A1 | 6/2009 | Cunningham et al. |
| 2009/0157071 A1 | 6/2009 | Wham et al. |
| 2009/0157072 A1 | 6/2009 | Wham et al. |
| 2009/0157075 A1 | 6/2009 | Wham et al. |
| 2009/0171350 A1 | 7/2009 | Dycus et al. |
| 2009/0171353 A1 | 7/2009 | Johnson et al. |
| 2009/0182327 A1 | 7/2009 | Unger |
| 2009/0182329 A1 | 7/2009 | Dycus |
| 2009/0187188 A1 | 7/2009 | Guerra et al. |
| 2009/0198233 A1 | 8/2009 | Chojin |
| 2009/0204114 A1 | 8/2009 | Odom |
| 2009/0209957 A1 | 8/2009 | Schmaltz et al. |
| 2009/0209960 A1 | 8/2009 | Chojin |
| 2009/0234354 A1 | 9/2009 | Johnson et al. |
| 2009/0248021 A1 | 10/2009 | McKenna |
| 2009/0261804 A1 | 10/2009 | McKenna et al. |
| 2009/0292282 A9 | 11/2009 | Dycus |
| 2009/0306660 A1 | 12/2009 | Johnson et al. |
| 2010/0016857 A1 | 1/2010 | McKenna et al. |
| 2010/0023009 A1 | 1/2010 | Moses et al. |
| 2010/0036375 A1 | 2/2010 | Regadas |
| 2010/0042100 A1 | 2/2010 | Tetzlaff et al. |
| 2010/0042140 A1 | 2/2010 | Cunningham |
| 2010/0042142 A1 | 2/2010 | Cunningham |
| 2010/0042143 A1 | 2/2010 | Cunningham |
| 2010/0049187 A1 | 2/2010 | Carlton et al. |
| 2010/0057081 A1 | 3/2010 | Hanna |
| 2010/0057082 A1 | 3/2010 | Hanna |
| 2010/0057083 A1 | 3/2010 | Hanna |
| 2010/0057084 A1 | 3/2010 | Hanna |
| 2010/0063500 A1 | 3/2010 | Muszala |
| 2010/0069903 A1 | 3/2010 | Allen, IV et al. |
| 2010/0069904 A1 | 3/2010 | Cunningham |
| 2010/0069953 A1 | 3/2010 | Cunningham et al. |
| 2010/0076427 A1 | 3/2010 | Heard |
| 2010/0076430 A1 | 3/2010 | Romero |
| 2010/0076431 A1 | 3/2010 | Allen, IV |
| 2010/0076432 A1 | 3/2010 | Horner |
| 2010/0087816 A1 | 4/2010 | Roy |
| 2010/0087818 A1 | 4/2010 | Cunningham |
| 2010/0094271 A1 | 4/2010 | Ward et al. |
| 2010/0094286 A1 | 4/2010 | Chojin |
| 2010/0094287 A1 | 4/2010 | Cunningham et al. |
| 2010/0100122 A1 | 4/2010 | Hinton |
| 2010/0130971 A1 | 5/2010 | Baily |
| 2010/0130977 A1 | 5/2010 | Garrison et al. |
| 2010/0145334 A1 | 6/2010 | Olson et al. |
| 2010/0145335 A1 | 6/2010 | Johnson et al. |
| 2010/0179539 A1 | 7/2010 | Nau, Jr. |
| 2010/0179543 A1 | 7/2010 | Johnson et al. |
| 2010/0179545 A1 | 7/2010 | Twomey et al. |
| 2010/0179546 A1 | 7/2010 | Cunningham |
| 2010/0179547 A1 | 7/2010 | Cunningham et al. |
| 2010/0198248 A1* | 8/2010 | Vakharia ................ 606/51 |
| 2010/0204697 A1 | 8/2010 | Dumbauld et al. |
| 2010/0204698 A1 | 8/2010 | Chapman et al. |
| 2010/0217258 A1 | 8/2010 | Floume et al. |
| 2010/0217264 A1 | 8/2010 | Odom et al. |
| 2010/0249769 A1 | 9/2010 | Nau, Jr. et al. |
| 2010/0249776 A1 | 9/2010 | Kerr |
| 2010/0256635 A1 | 10/2010 | McKenna et al. |
| 2010/0274244 A1 | 10/2010 | Heard |
| 2010/0280511 A1 | 11/2010 | Rachlin et al. |
| 2010/0280515 A1 | 11/2010 | Hixson et al. |
| 2010/0286691 A1 | 11/2010 | Kerr et al. |
| 2010/0307934 A1 | 12/2010 | Chowaniec et al. |
| 2010/0312235 A1 | 12/2010 | Bahney |
| 2010/0312238 A1 | 12/2010 | Schechter et al. |
| 2010/0312242 A1 | 12/2010 | Odom |
| 2010/0331839 A1 | 12/2010 | Schechter et al. |
| 2011/0004209 A1 | 1/2011 | Lawes et al. |
| 2011/0004210 A1 | 1/2011 | Johnson et al. |
| 2011/0009864 A1 | 1/2011 | Bucciaglia et al. |
| 2011/0015632 A1 | 1/2011 | Artale |

FOREIGN PATENT DOCUMENTS

| | | |
|---|---|---|
| CA | 2 520 413 | 3/2007 |
| DE | 2415263 | 10/1975 |
| DE | 2514501 | 10/1976 |
| DE | 2627679 | 1/1977 |
| DE | 3423356 | 1/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 4/2002 |
| DE | 10 2004 026 179 | 12/2005 |
| DE | 20 2007 009165 | 10/2007 |
| DE | 20 2007 009317 | 10/2007 |
| DE | 19738457 | 1/2009 |
| EP | 0364216 | 4/1990 |
| EP | 0467501 | 1/1992 |
| EP | 0509670 | 10/1992 |
| EP | 0518230 | 12/1992 |
| EP | 0541930 | 5/1993 |
| EP | 0306123 | 8/1993 |
| EP | 0572131 | 12/1993 |
| EP | 0584787 | 3/1994 |
| EP | 0589453 | 3/1994 |
| EP | 0589555 | 3/1994 |
| EP | 0623316 | 11/1994 |
| EP | 0624348 | 11/1994 |
| EP | 0650701 | 5/1995 |
| EP | 0694290 | 3/1996 |
| EP | 0717966 | 6/1996 |
| EP | 0754437 | 3/1997 |
| EP | 0517243 | 9/1997 |
| EP | 0853922 | 7/1998 |
| EP | 0875209 | 11/1998 |
| EP | 0878169 | 11/1998 |
| EP | 0887046 | 1/1999 |
| EP | 0923907 | 6/1999 |
| EP | 0950378 | 10/1999 |
| EP | 0986990 | 3/2000 |
| EP | 1034747 | 9/2000 |
| EP | 1034748 | 9/2000 |
| EP | 1025807 | 10/2000 |
| EP | 1034746 | 10/2000 |
| EP | 1050278 | 11/2000 |
| EP | 1053719 | 11/2000 |

| | | | | | |
|---|---|---|---|---|---|
| EP | 1053720 | 11/2000 | WO | WO 96/05776 | 2/1996 |
| EP | 1055399 | 11/2000 | WO | WO 96/11635 | 4/1996 |
| EP | 1055400 | 11/2000 | WO | WO 96/22056 | 7/1996 |
| EP | 1080694 | 3/2001 | WO | WO 96/13218 | 9/1996 |
| EP | 1082944 | 3/2001 | WO | WO 97/00646 | 1/1997 |
| EP | 1159926 | 12/2001 | WO | WO 97/00647 | 1/1997 |
| EP | 1177771 | 2/2002 | WO | WO 97/10764 | 3/1997 |
| EP | 1278007 | 1/2003 | WO | WO 97/18768 | 5/1997 |
| EP | 1301135 | 4/2003 | WO | WO 97/24073 | 7/1997 |
| EP | 1330991 | 7/2003 | WO | WO 97/24993 | 7/1997 |
| EP | 1486177 | 6/2004 | WO | WO 98/14124 | 4/1998 |
| EP | 1472984 | 11/2004 | WO | WO 98/27880 | 7/1998 |
| EP | 0774232 | 1/2005 | WO | WO 98/31290 | 7/1998 |
| EP | 1527747 | 5/2005 | WO | WO 98/43264 | 10/1998 |
| EP | 1530952 | 5/2005 | WO | WO 99/03407 | 1/1999 |
| EP | 1532932 | 5/2005 | WO | WO 99/03408 | 1/1999 |
| EP | 1535581 | 6/2005 | WO | WO 99/03409 | 1/1999 |
| EP | 1609430 | 12/2005 | WO | WO 99/03414 | 1/1999 |
| EP | 1201192 | 2/2006 | WO | WO 99/12488 | 3/1999 |
| EP | 1632192 | 3/2006 | WO | WO 99/23933 | 5/1999 |
| EP | 1642543 | 4/2006 | WO | WO 99/40857 | 8/1999 |
| EP | 1645238 | 4/2006 | WO | WO 99/40861 | 8/1999 |
| EP | 1645240 | 4/2006 | WO | WO 99/51158 | 10/1999 |
| EP | 1649821 | 4/2006 | WO | WO 99/66850 | 12/1999 |
| EP | 1707143 | 10/2006 | WO | WO 00/24330 | 5/2000 |
| EP | 1545360 | 3/2007 | WO | WO 00/24331 | 5/2000 |
| EP | 1767163 | 3/2007 | WO | WO 00/33753 | 6/2000 |
| EP | 1769765 | 4/2007 | WO | WO 00/36986 | 6/2000 |
| EP | 1769766 | 4/2007 | WO | WO 00/41638 | 7/2000 |
| EP | 1785097 | 5/2007 | WO | WO 00/47124 | 8/2000 |
| EP | 1785098 | 5/2007 | WO | WO 00/53112 | 9/2000 |
| EP | 1785101 | 5/2007 | WO | WO 01/01847 | 1/2001 |
| EP | 1810625 | 7/2007 | WO | WO 01/15614 | 3/2001 |
| EP | 1810628 | 7/2007 | WO | WO 01/17448 | 3/2001 |
| EP | 1842500 | 10/2007 | WO | WO 01/54604 | 8/2001 |
| EP | 1878400 | 1/2008 | WO | WO 02/07627 | 1/2002 |
| EP | 1929970 | 6/2008 | WO | WO 02/067798 | 9/2002 |
| EP | 1990019 | 11/2008 | WO | WO 02/080783 | 10/2002 |
| EP | 1683496 | 12/2008 | WO | WO 02/080784 | 10/2002 |
| EP | 1997438 | 12/2008 | WO | WO 02/080785 | 10/2002 |
| EP | 1997439 | 12/2008 | WO | WO 02/080786 | 10/2002 |
| EP | 1527744 | 2/2009 | WO | WO 02/080793 | 10/2002 |
| EP | 2206474 | 7/2010 | WO | WO 02/080794 | 10/2002 |
| GB | 623316 | 5/1949 | WO | WO 02/080795 | 10/2002 |
| GB | 1490585 | 11/1977 | WO | WO 02/080796 | 10/2002 |
| GB | 2214430 A | 6/1989 | WO | WO 02/080797 | 10/2002 |
| GB | 2213416 A | 8/1989 | WO | WO 02/080798 | 10/2002 |
| JP | 61-501068 | 9/1984 | WO | WO 02/080799 | 10/2002 |
| JP | 6-502328 | 3/1992 | WO | WO 02/081170 | 10/2002 |
| JP | 5-5106 | 1/1993 | WO | WO 03/061500 | 7/2003 |
| JP | 5-40112 | 2/1993 | WO | WO 03/090630 | 11/2003 |
| JP | 06343644 | 12/1994 | WO | WO 03/101311 | 12/2003 |
| JP | 07265328 | 10/1995 | WO | WO 2004/028585 | 4/2004 |
| JP | 08056955 | 3/1996 | WO | WO 2004/032776 | 4/2004 |
| JP | 08252263 | 10/1996 | WO | WO 2004/032777 | 4/2004 |
| JP | 09010223 | 1/1997 | WO | WO 2004/052221 | 6/2004 |
| JP | 10-24051 | 1/1998 | WO | WO 2004/073488 | 9/2004 |
| JP | 11-070124 | 5/1998 | WO | WO 2004/073490 | 9/2004 |
| JP | 2000-102545 | 9/1998 | WO | WO 2004/073753 | 9/2004 |
| JP | 11-169381 | 6/1999 | WO | WO 2004/082495 | 9/2004 |
| JP | 11244298 | 9/1999 | WO | WO 2004/098383 | 11/2004 |
| JP | 2000-342599 | 12/2000 | WO | WO 2004/103156 | 12/2004 |
| JP | 2000-350732 | 12/2000 | WO | WO 2005/004734 | 1/2005 |
| JP | 2001-008944 | 1/2001 | WO | WO 2005/004735 | 1/2005 |
| JP | 2001-029356 | 2/2001 | WO | WO 2005/009255 | 2/2005 |
| JP | 2001-128990 | 5/2001 | WO | WO 2005/048809 | 6/2005 |
| SU | 401367 | 11/1974 | WO | WO 2005/050151 | 6/2005 |
| WO | WO 89/00757 | 1/1989 | WO | WO 2005/110264 | 11/2005 |
| WO | WO 92/04873 | 4/1992 | WO | WO 2008/008457 | 1/2008 |
| WO | WO 92/06642 | 4/1992 | WO | WO 2008/040483 | 4/2008 |
| WO | WO 93/19681 | 10/1993 | WO | WO 2008/045348 | 4/2008 |
| WO | WO 93/21845 | 11/1993 | WO | WO 2008/045350 | 4/2008 |
| WO | WO 94/00059 | 1/1994 | WO | WO 2008/112147 | 9/2008 |
| WO | WO 94/08524 | 4/1994 | WO | WO 2009/005850 | 1/2009 |
| WO | WO 94/20025 | 9/1994 | WO | WO 2009/039179 | 3/2009 |
| WO | WO 95/02369 | 1/1995 | WO | WO 2009/039510 | 3/2009 |
| WO | WO 95/07662 | 3/1995 | | | |
| WO | WO 95/15124 | 6/1995 | | | |
| WO | WO 95/20360 | 8/1995 | | | |

OTHER PUBLICATIONS

U.S. Appl. No. 09/591,328, filed Jun. 9, 2000.
U.S. Appl. No. 12/336,970, filed Dec. 17, 2008.
U.S. Appl. No. 12/535,869, filed Aug. 5, 2009.
U.S. Appl. No. 12/543,831, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/568,838, filed Sep. 29, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/597,213, filed Oct. 23, 2009.
U.S. Appl. No. 12/607,191, filed Oct. 28, 2009.
U.S. Appl. No. 12/619,100, filed Nov. 16, 2009.
U.S. Appl. No. 12/692,414, filed Jan. 22, 2010.
U.S. Appl. No. 12/696,592, filed Jan. 29, 2010.
U.S. Appl. No. 12/696,857, filed Jan. 29, 2010.
U.S. Appl. No. 12/700,856, filed Feb. 5, 2010.
U.S. Appl. No. 12/719,407, filed Mar. 8, 2010.
U.S. Appl. No. 12/728,994, filed Mar. 22, 2010.
U.S. Appl. No. 12/748,028, filed Mar. 26, 2010.
U.S. Appl. No. 12/757,340, filed Apr. 9, 2010.
U.S. Appl. No. 12/758,524, filed Apr. 12, 2010.
U.S. Appl. No. 12/759,551, filed Apr. 13, 2010.
U.S. Appl. No. 12/769,444, filed Apr. 28, 2010.
U.S. Appl. No. 12/770,369, filed Apr. 29, 2010.
U.S. Appl. No. 12/770,380, filed Apr. 29, 2010.
U.S. Appl. No. 12/770,387, filed Apr. 29, 2010.
U.S. Appl. No. 12/773,526, filed May 4, 2010.
U.S. Appl. No. 12/773,644, filed May 4, 2010.
U.S. Appl. No. 12/786,589, filed May 25, 2010.
U.S. Appl. No. 12/791,112, filed Jun. 1, 2010.
U.S. Appl. No. 12/792,001, filed Jun. 2, 2010.
U.S. Appl. No. 12/792,008, filed Jun. 2, 2010.
U.S. Appl. No. 12/792,019, filed Jun. 2, 2010.
U.S. Appl. No. 12/792,038, filed Jun. 2, 2010.
U.S. Appl. No. 12/792,051, filed Jun. 2, 2010.
U.S. Appl. No. 12/792,068, filed Jun. 2, 2010.
U.S. Appl. No. 12/792,097, filed Jun. 2, 2010.
U.S. Appl. No. 12/792,262, filed Jun. 2, 2010.
U.S. Appl. No. 12/792,299, filed Jun. 2, 2010.
U.S. Appl. No. 12/792,330, filed Jun. 2, 2010.
U.S. Appl. No. 12/822,024, filed Jun. 23, 2010.
U.S. Appl. No. 12/821,253, filed Jun. 23, 2010.
U.S. Appl. No. 12/832,772, filed Jul. 8, 2010.
U.S. Appl. No. 12/843,384, filed Jul. 26, 2010.
U.S. Appl. No. 12/845,203, filed Jul. 28, 2010.
U.S. Appl. No. 12/853,896, filed Aug. 10, 2010.
U.S. Appl. No. 12/859,896, filed Aug. 20, 2010.
U.S. Appl. No. 12/861,198, filed Aug. 23, 2010.
U.S. Appl. No. 12/861,209, filed Aug. 23, 2010.
U.S. Appl. No. 12/876,668, filed Sep. 7, 2010.
U.S. Appl. No. 12/876,680, filed Sep. 7, 2010.
U.S. Appl. No. 12/876,705, filed Sep. 7, 2010.
U.S. Appl. No. 12/876,731, filed Sep. 7, 2010.
U.S. Appl. No. 12/877,199, filed Sep. 8, 2010.
U.S. Appl. No. 12/877,482, filed Sep. 8, 2010.
U.S. Appl. No. 12/895,020, filed Sep. 30, 2010.
U.S. Appl. No. 12/896,100, filed Oct. 1, 2010.
U.S. Appl. No. 12/897,346, filed Oct. 4, 2010.
U.S. Appl. No. 12/899,304, filed Oct. 6, 2010.
U.S. Appl. No. 12/906,672, filed Oct. 18, 2010.
U.S. Appl. No. 12/915,809, filed Oct. 29, 2010.
U.S. Appl. No. 12/947,352, filed Nov. 16, 2010.
U.S. Appl. No. 12/947,420, filed Nov. 16, 2010.
U.S. Appl. No. 12/948,081, filed Nov. 17, 2010.
U.S. Appl. No. 12/948,144, filed Nov. 17, 2010.
U.S. Appl. No. 12/950,505, filed Nov. 19, 2010.
U.S. Appl. No. 12/950,791, filed Nov. 19, 2010.
U.S. Appl. No. 12/955,010, filed Nov. 29, 2010.
U.S. Appl. No. 12/955,042, filed Nov. 29, 2010.
U.S. Appl. No. 12/981,771, filed Dec. 30, 2010.
U.S. Appl. No. 12/981,787, filed Dec. 30, 2010.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998),12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

Benaron et al., "Optical Time-of-Flight and Absorbance Imaging of Biologic Media", Science, American Association for the Advancement of Science, Washington, DC, vol. 259, Mar. 5, 1993, pp. 1463-1466.

Olsson et al. "Radical Cystectomy in Females" Current Surgical Techniques in Urology, vol. 14, Issue 3, 2001.

Palazzo et al. "Randomized clinical trial of Ligasure versus open haemorrhoidectomy" British Journal of Surgery 2002, 89, 154-157.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

"Reducing Needlestick Injuries in the Operating Room" Sales/Product Literature 2001.

Bergdahl et al. "Studies on Coagulation and the Development of an Automatic Computerized Bipolar Coagulator" J.Neurosurg, vol. 75, Jul. 1991, pp. 148-151.

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.

Sayfan et al. "Sutureless Closed Hemorrhoidectomy: A New Technique" Annals of Surgery vol. 234 No. 1 Jul. 2001; pp. 21-24.

Levy et al., "Update on Hysterectomy—New Technologies and Techniques" OBG Management, Feb. 2003.

Dulemba et al. "Use of a Bipolar Electrothermal Vessel Sealer in Laparoscopically Assisted Vaginal Hysterectomy" Sales/Product Literature; Jan. 2004.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Sengupta et al., "Use of a Computer-Controlled Bipolar Diathermy System in Radical Prostatectomies and Other Open Urological Surgery" ANZ Journal of Surgery (2001) 71.9 pp. 538-540.

Rothenberg et al. "Use of the LigaSure Vessel Sealing System in Minimally Invasive Surgery in Children" Int'l Pediatric Endosurgery Group (IPEG) 2000.

Crawford et al. "Use of the LigaSure Vessel Sealing System in Urologic Cancer Surgery" Grand Rounds in Urology 1999 vol. 1 Issue 4 pp. 10-17.

Craig Johnson, "Use of the LigaSure Vessel Sealing System in Bloodless Hemorrhoidectomy" Innovations That Work, Mar. 2000.

Levy et al. "Use of a New Energy-based Vessel Ligation Device During Vaginal Hysterectomy" Int'l Federation of Gynecology and Obstetrics (FIGO) World Congress 1999.

Barbara Levy, "Use of a New Vessel Ligation Device During Vaginal Hysterectomy" FIGO 2000, Washington, D.C.

E. David Crawford "Use of a Novel Vessel Sealing Technology in Management of the Dorsal Veinous Complex" Sales/Product Literature 2000.

Jarrett et al., "Use of the LigaSure Vessel Sealing System for Peri-Hilar Vessels in Laparoscopic Nephrectomy" Sales/Product Literature 2000.

Crouch et al. "A Velocity-Dependent Model for Needle Insertion in Soft Tissue" MICCAI 2005; LNCS 3750 pp. 624-632, Dated: 2005.

McLellan et al. "Vessel Sealing for Hemostasis During Pelvic Surgery" Int'l Federation of Gynecology and Obstetrics FIGO World Congress 2000, Washington, D.C.

McLellan et al. "Vessel Sealing for Hemostasis During Gynecologic Surgery" Sales/Product Literature 1999.

Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.

Int'l Search Report EP 09 172749.5 dated Dec. 4, 2009.
Int'l Search Report EP 10 000259.1 dated Jun. 30, 2010.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534dated Dec. 19, 2003.
Int'l Search Report PCT/US04/03436 dated Mar. 3, 2005.
Int'l Search Report PCT/USO4/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
Examiner's First Report from Australian Patent Application No. 2005225098 mailed Jun. 24, 2010.
European Search Report for European Application No. 10182019 dated Aug. 22, 2011.

* cited by examiner

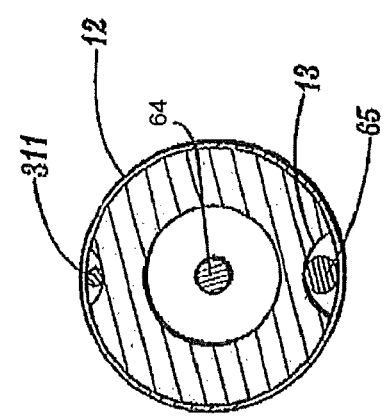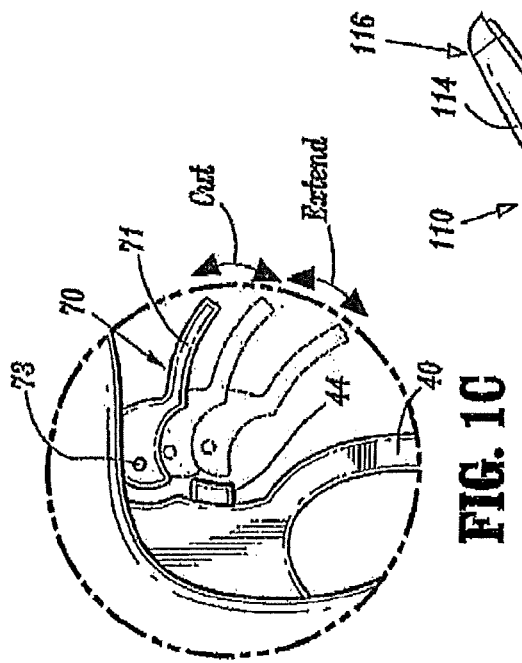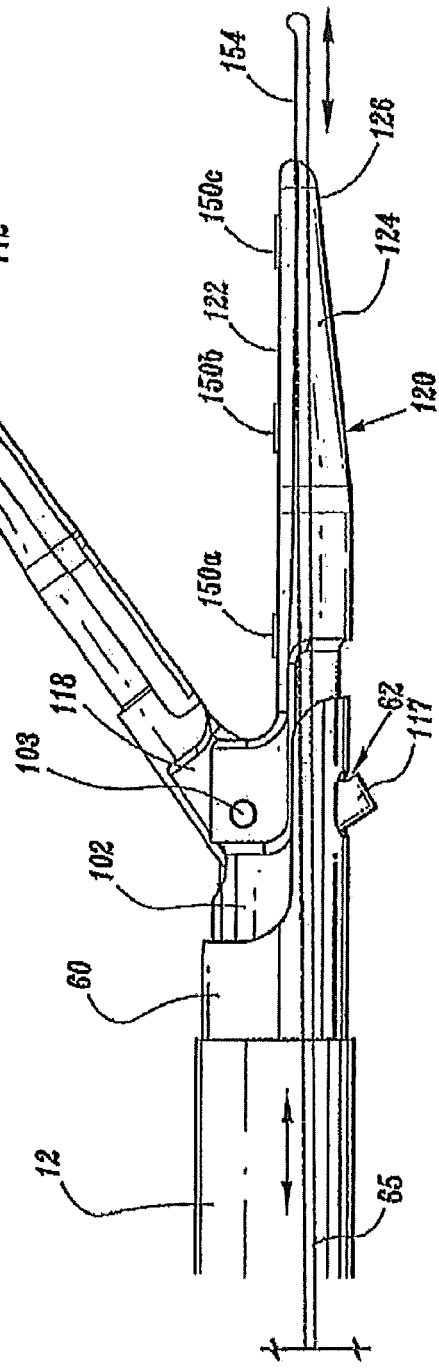

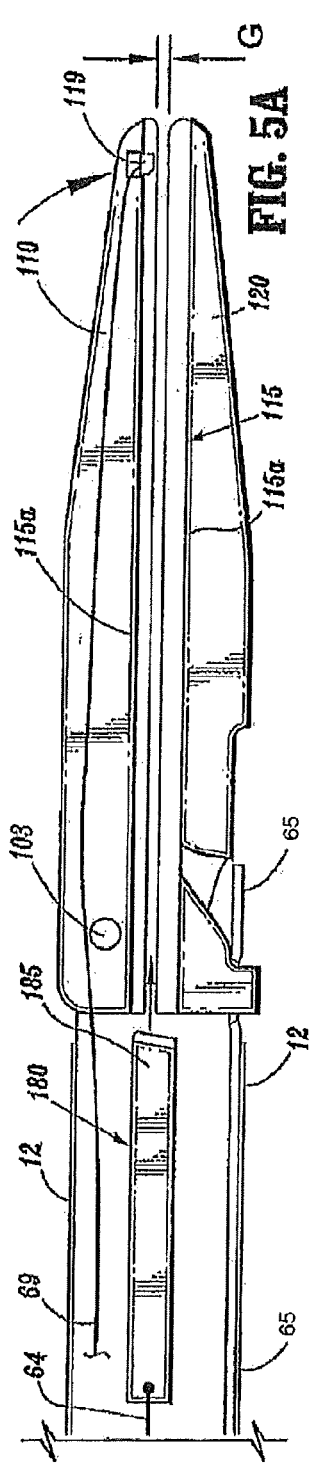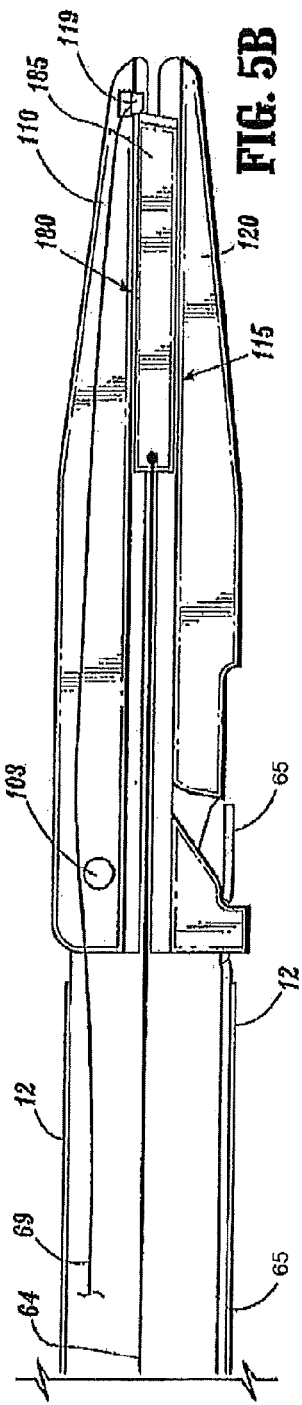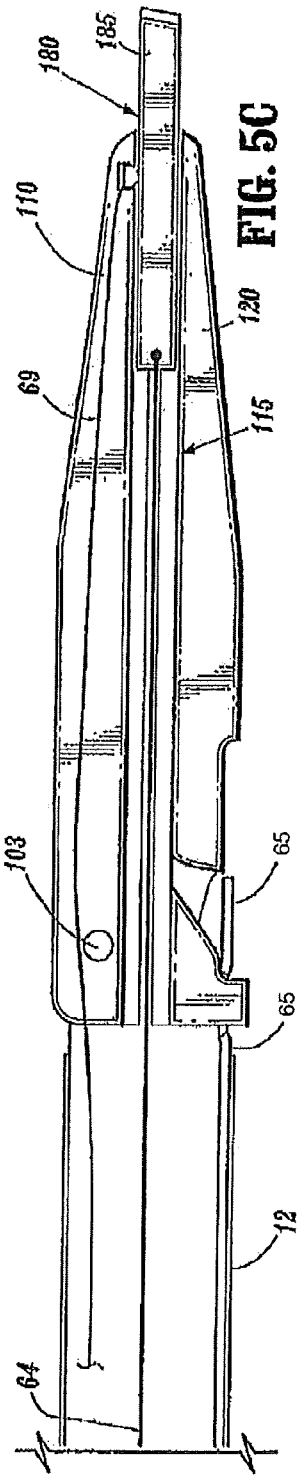

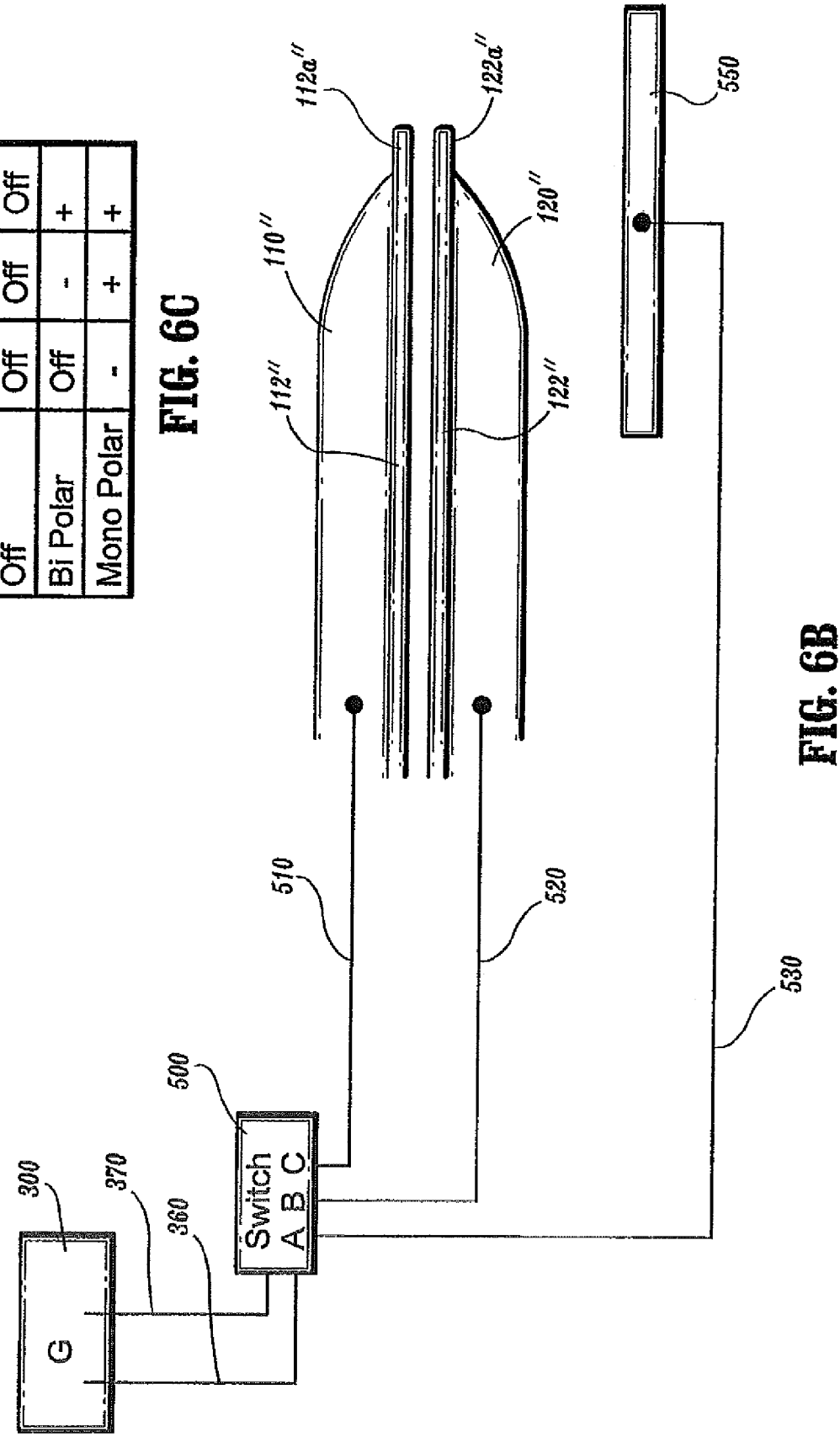

BIPOLAR FORCEPS HAVING MONOPOLAR EXTENSION

CROSS REFERENCE TO RELATED APPLICATIONS

This application is a divisional of U.S. patent application Ser. No. 11/904,123 filed on Sep. 26, 2007 now abandoned, which is a divisional of U.S. patent application Ser. No. 10/988,950 entitled "BIPOLAR FORCEPS HAVING MONOPOLAR EXTENSION" filed on Nov. 15, 2004 now U.S. Pat. No. 7,367,976 by Lawes et al. which claims the benefits of and priority to U.S. Provisional Application Ser. No. 60/520,579 filed on Nov. 17, 2003 by Lawes et al. entitled "BIPOLAR FORCEPS HAVING MONOPOLAR EXTENSION," the entire contents of each of which being incorporated by reference herein.

BACKGROUND

The present disclosure relates to an electrosurgical forceps and more particularly, the present disclosure relates to an endoscopic bipolar electrosurgical forceps for coagulating, sealing and/or cutting tissue having a selectively energizable and/or extendable monopolar extension for enhanced electrosurgical effect.

Technical Field

Electrosurgical forceps utilize both mechanical clamping action and electrical energy to effect hemostasis by heating the tissue and blood vessels to coagulate, cauterize and/or seal tissue. As an alternative to open forceps for use with open surgical procedures, many modern surgeons use endoscopes and endoscopic instruments for remotely accessing organs through smaller, puncture-like incisions. As a direct result thereof, patients tend to benefit from less scarring and reduced healing time.

Endoscopic instruments are inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make endoscopic instruments that fit through the smaller cannulas.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an electrosurgical scissors, the surgeon may cut tissue during a given surgical procedure utilizing a combination of mechanical cutting action and electrosurgical cutting. By utilizing an endoscopic electrosurgical forceps, a surgeon can cauterize, coagulate/desiccate and/or simply reduce or slow bleeding simply by controlling the intensity, frequency and duration of the electrosurgical energy applied through the jaw members to the tissue.

For treating larger vessels, a surgeon may opt to seal the tissue or vessel. Tissue sealing is fundamentally different than simply coagulating or cauterizing vessels. For the purposes herein, "coagulation" is defined as a process of desiccating tissue wherein the tissue cells are ruptured and dried. "Vessel sealing" or "tissue sealing" is defined as the process of liquefying the collagen in the tissue so that it reforms into a fused mass with limited demarcation between adjacent tissue structures. In order to effectively seal larger vessels (or tissue) two predominant mechanical parameters must be accurately controlled—the pressure applied to the vessel (tissue) preferably about 3 kg/cm$^2$ to about 16 kg/cm$^2$ and the gap distance between the electrodes preferably about 0.001 inches to about 0.006 inches. Several examples of endoscopic vessel sealing instruments are disclosed in commonly-owned U.S. patent application Ser. Nos. 10/116,944, 10/179,863, 101369,894 and 10/180,926 and PCT/US01/11340 the entire contents of all of which are hereby incorporated by reference herein.

Generally, the electrical configuration of electrosurgical forceps can be categorized in two classifications: 1) monopolar electrosurgical forceps; and 2) bipolar electrosurgical forceps. Monopolar forceps utilize one active electrode associated with the clamping end effector and a remote patient return electrode or pad which is attached externally to the patient. When the electrosurgical energy is applied, the energy travels from the active electrode, to the surgical site, through the patient and to the return electrode.

Bipolar electrosurgical forceps utilize two generally opposing electrodes which are disposed on the inner opposing surfaces of end effectors and which are both electrically coupled to an electrosurgical generator. Each electrode is charged to a different electric potential. Since tissue is a conductor of electrical energy, when the effectors are utilized to grasp, seal or cut tissue therebetween, the electrical energy can be selectively transferred through the tissue.

One of the inherent disadvantages to utilizing a bipolar endoscopic forceps for cauterizing, coagulating cutting or sealing vessels and other tissues is the inability of the bipolar forceps to match the benefits or advantages of monopolar instruments (i.e., monopolar instruments have the ability to move through avascular tissue and dissect through narrow tissue planes) necessitating the need for the surgeon to replace the bipolar forceps during surgery to reap the benefits of using the monopolar instrument for certain applications. Likewise, during some monopolar endoscopic applications it may be advantageous to replace the monopolar instrument with a bipolar forceps, e.g., for sealing large tissue structures. For example, during a cholecystectomy the gallbladder is dissected from the liver which would typically entail using an endoscopic monopolar instrument, e.g., electrosurgical blade, electrosurgical pencil, loop electrode, etc. However, during the cholecystectomy procedure there may also be a need to seal the cystic duct or cystic artery which may require a bipolar vessel sealing instrument necessitating the need to replace the monopolar instrument. The surgeon may need to repeatedly remove the monopolar instrument from the operating cavity to utilize the bipolar instrument and vice versa.

Thus there exists a need to develop an instrument which can combine the benefits of both monopolar and bipolar operation thereby reducing the need for the surgeon to substitute instruments during surgical certain procedures.

SUMMARY

The present disclosure relates to an endoscopic forceps for treating tissue and includes a housing having a shaft affixed thereto and first and second jaw members attached to a distal end of the shaft. The forceps also includes an actuator for moving jaw members relative to one another from a first position wherein the jaw members are disposed in spaced relation relative to one another to a second position wherein the jaw members cooperate to grasp tissue therebetween. A source of electrosurgical energy is connected to each jaw member such that the jaw members are selectively capable of operating in a bipolar mode which enables the jaw members to conduct bipolar energy through tissue held therebetween to treat tissue. The forceps also includes a monopolar element housed within at least the first jaw member which is selectively movable from a first position within the first jaw member to a second position distal to the first jaw member. The monopolar element is connected to the source of electrosurgical energy and is selectively activateable independent of the jaw members.

In one embodiment according to the present disclosure, the forceps includes a knife which is selectively moveable within a knife channel defined within at least one of the first and second jaw members to cut tissue disposed between the first and second jaw members. Advantageously, a knife actuator allows a user to selectively move the knife to cut tissue disposed between the jaw members. The source of electrosurgical energy carries electrical potentials to each respective jaw member such that the jaw members are capable of conducting bipolar energy through tissue held therebetween to effect a tissue seal.

Advantageously, the knife is designed to initially cut tissue disposed between the first and second jaw members and subsequently extend distally from the jaw members to treat tissue in a monopolar fashion. Preferably, the forceps includes a safety (e.g. a safety circuit or mechanical safety element) which only allows electrical activation of the knife (or monopolar element) when the knife (or monopolar element) is extended from the distal ends of the jaw members. The safety may also deactivate the jaw members through circuitry or utilizing a mechanical safety element.

In one embodiment, the first jaw member and the second jaw member each include an elongated slot which runs in opposition substantially along the respective lengths thereof such that the two opposing elongated slots form the knife channel for reciprocating the knife to divide tissue disposed between the two jaw members.

In another embodiment, the forceps is a vessel sealing forceps and at least one of the jaw members includes at least one non-conductive stop member disposed thereon which controls the distance between the first and second jaw members when tissue is held therebetween. Advantageously, the stop member(s) maintains a gap distance of about 0.001 inches to about 0.006 inches between the jaw members when tissue is compressed between the jaw members.

In yet another embodiment according to the present disclosure, the forceps includes an actuator which operates to both move the knife to cut tissue disposed between jaw members and to extend the knife or a separate monopolar element from the first position within the first jaw member to the second position distal to the first jaw member. In still yet another embodiment according to the present disclosure, the forceps includes an actuator which operates to both move the jaw members relative to one another from the first to second positions to grasp tissue therebetween and to extend the monopolar element from the first position within the first jaw member to the second position distal to the first jaw member.

In another embodiment according to the present disclosure, a first actuator may be designed to operate the jaw members for grasping tissue and a second actuator may be included which operates to extend the monopolar element from the first position within the first jaw member to the second position distal to the first jaw member.

The present disclosure also relates to an endoscopic forceps which includes a housing having a shaft affixed thereto and first and second jaw members attached to a distal end of the shaft. The first jaw member is configured to extend distally relative to the second jaw member. A actuator is includes for moving jaw members relative to one another from a first position wherein the jaw members are disposed in spaced relation relative to one another to a second position wherein the jaw members cooperate to grasp tissue therebetween. The jaw members are connected to a source of electrosurgical energy such that the jaw members are selectively capable of operating in a bipolar mode which enables the jaw members to conduct bipolar energy through tissue held therebetween.

The forceps also includes a control switch which, upon selective activation, deactivates the second jaw member and activates the first jaw member with a first electrical potential. At relatively the same time, the control switch also activates a return electrode or return pad with a different electrical potential which is placed adjacent to the patient to enable the first jaw member to selectively treat tissue in a monopolar fashion. Preferably, a safety is included which limits electrical activation of the control switch to when the jaw members are disposed in the second position.

The present disclosure also relates to an endoscopic forceps which includes a housing having a shaft affixed thereto. The shaft includes first and second jaw members attached to a distal end thereof. Preferably, the first and second jaw members each include a tapered or elongated distal end.

The forceps also includes an actuator for moving jaw members relative to one another from a first position wherein the jaw members are disposed in spaced relation relative to one another to a second position wherein the jaw members cooperate to grasp tissue therebetween. A source of electrosurgical energy is connected to each jaw member such that the jaw members are selectively capable of operating in a bipolar mode which enables the jaw members to conduct bipolar energy through tissue held therebetween.

A control switch is also included which, upon selective activation thereof, activates the first jaw member and the second jaw member with a first electrical potential and activates a return electrode with a different electrical potential. The return electrode is preferably placed adjacent to the patient which enables the first and second jaw members to selectively treat tissue in a monopolar fashion. Preferably, the forceps includes a safety which only allows electrical activation of the control switch when the jaw members are disposed in the second position.

In another embodiment of the present disclosure, the actuator is selectively lockable to maintain a closure pressure in the range of about 3 kg/cm$^2$ to about 16 kg/cm$^2$ and, preferably, about 7 kg/cm$^2$ to about 13 kg/cm$^2$ between the jaw members which is advantageous in producing effective and reliable tissue seals. In yet another embodiment, the forceps may also include a rotating assembly for rotating the jaw members about a longitudinal axis defined through the shaft. Advantageously, the forceps includes a unilateral jaw assembly, i.e., the first jaw member is movable relative to the second jaw member and the second jaw member is substantially fixed. Alternatively, the forceps may include a bilateral jaw assembly, i.e., both jaw members move relative to one another.

Preferably, a spring is included with the actuator or drive assembly to facilitate actuation of the movable handle and to assure the closure force is maintained within a working range of about 3 kg/cm$^2$ to about 16 kg/cm$^2$.

The present disclosure also relates to a method for treating tissue with electrosurgical energy from an electrosurgical generator which includes the steps of: providing an endoscopic forceps including a housing having a shaft affixed thereto. The shaft includes first and second jaw members attached to a distal end thereof. An actuator is included for moving jaw members relative to one another from a first position wherein the jaw members are disposed in spaced relation relative to one another to a second position wherein the jaw members cooperate to grasp tissue therebetween. A monopolar element is also included which is housed within at least the first jaw member and selectively movable from a first position within the first jaw member to a second position distal to the first jaw member. A return electrode is provided and placed in contact with patient tissue.

The method also includes the steps of: connecting to each jaw member, the monopolar element and the return electrode to the electrosurgical generator; grasping tissue between the jaw members; selectively activating the jaw members to treat tissue disposed between the jaw members in a bipolar fashion; and selectively activating the monopolar element and the return electrode independent of the jaw members to treat tissue in a monopolar fashion.

Preferably, after the step of selectively activating the jaw members to treat tissue, the method includes the step of: extending the monopolar element from the distal end of the jaw members. Advantageously, the step of selectively activating the monopolar element includes deactivating the jaw members.

After the step of selectively activating the jaw members to treat tissue, the method may include the step of: releasing the tissue from the jaw members.

BRIEF DESCRIPTION OF THE DRAWINGS

Various embodiments of the subject instrument are described herein with reference to the drawings wherein:

FIG. 1B is an enlarged, cross section taken along line 1B-1B of FIG. 1A;

FIG. 1C is an enlarged, side view of the trigger assembly of FIG. 1A;

FIG. 1D is an enlarged, side view of the embodiment of an end effector assembly of FIG. 1A showing relative extension of a monopolar element from a distal end of the end effector assembly;

FIG. 5A is an enlarged, side schematic view of one embodiment of an end effector assembly showing relative movement of a first jaw member relative to a second jaw member prior to advancement of the knife through the end effector assembly;

FIG. 5B is an enlarged, side schematic view of the end effector assembly showing relative movement of the knife through the end effector assembly to divide tissue;

FIG. 5C is an enlarged, side schematic view of the end effector assembly showing relative movement of the knife extending from the distal end of the end effector assembly;

FIG. 6B is schematic view of another embodiment of an end effector assembly showing a series of electrical connections to a control switch and a generator to enable both bipolar activation and monopolar activation; and FIG. 6C is a table showing the various modes of operation of the forceps utilizing the end effector configuration of FIG. 6B.

DETAILED DESCRIPTION

Figure 1A:
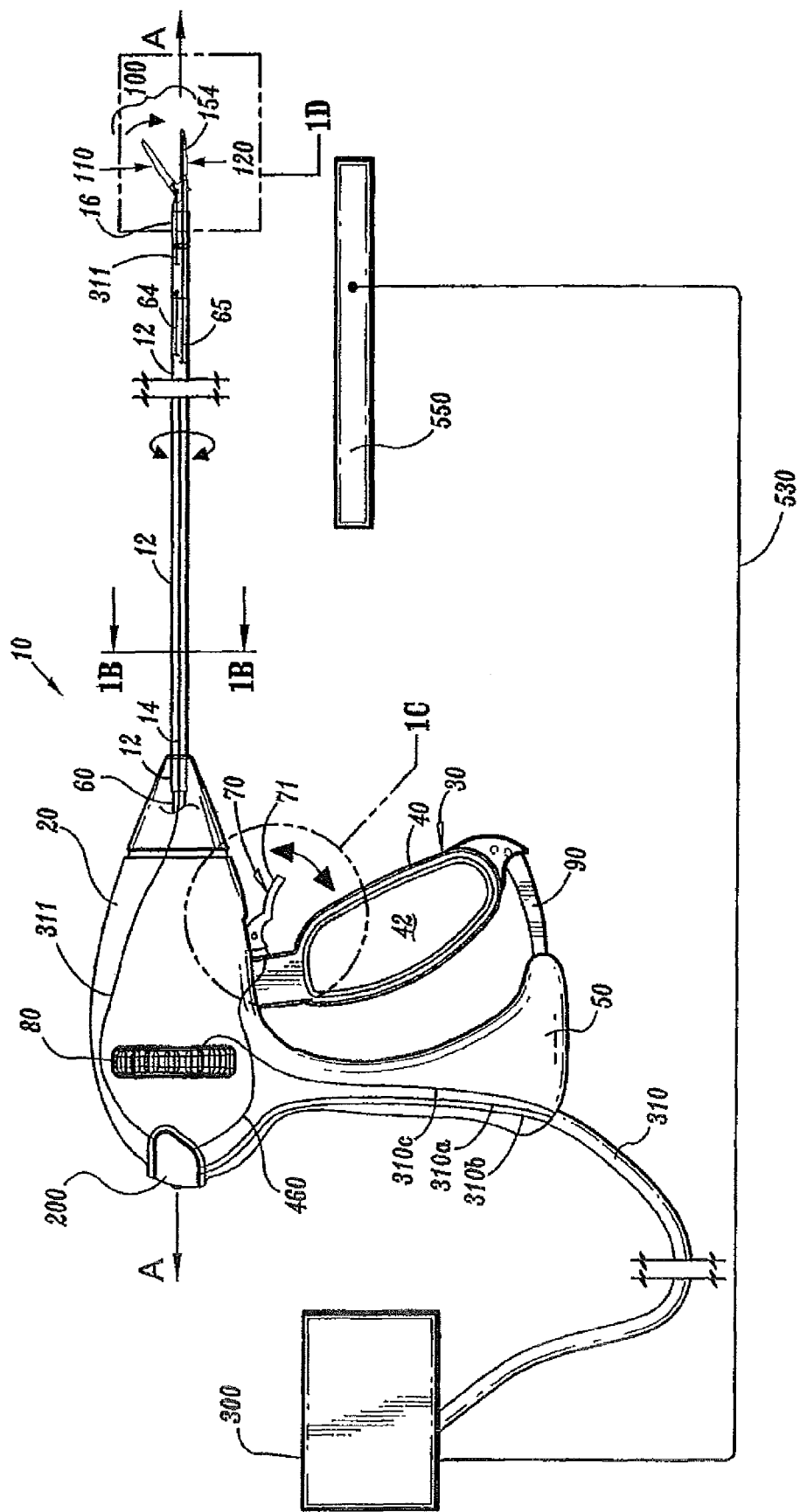
FIG. 1A is a side view of an endoscopic forceps showing a housing, a shaft, an end effector assembly and a trigger assembly in a first position according to the present disclosure.
Figure 2:
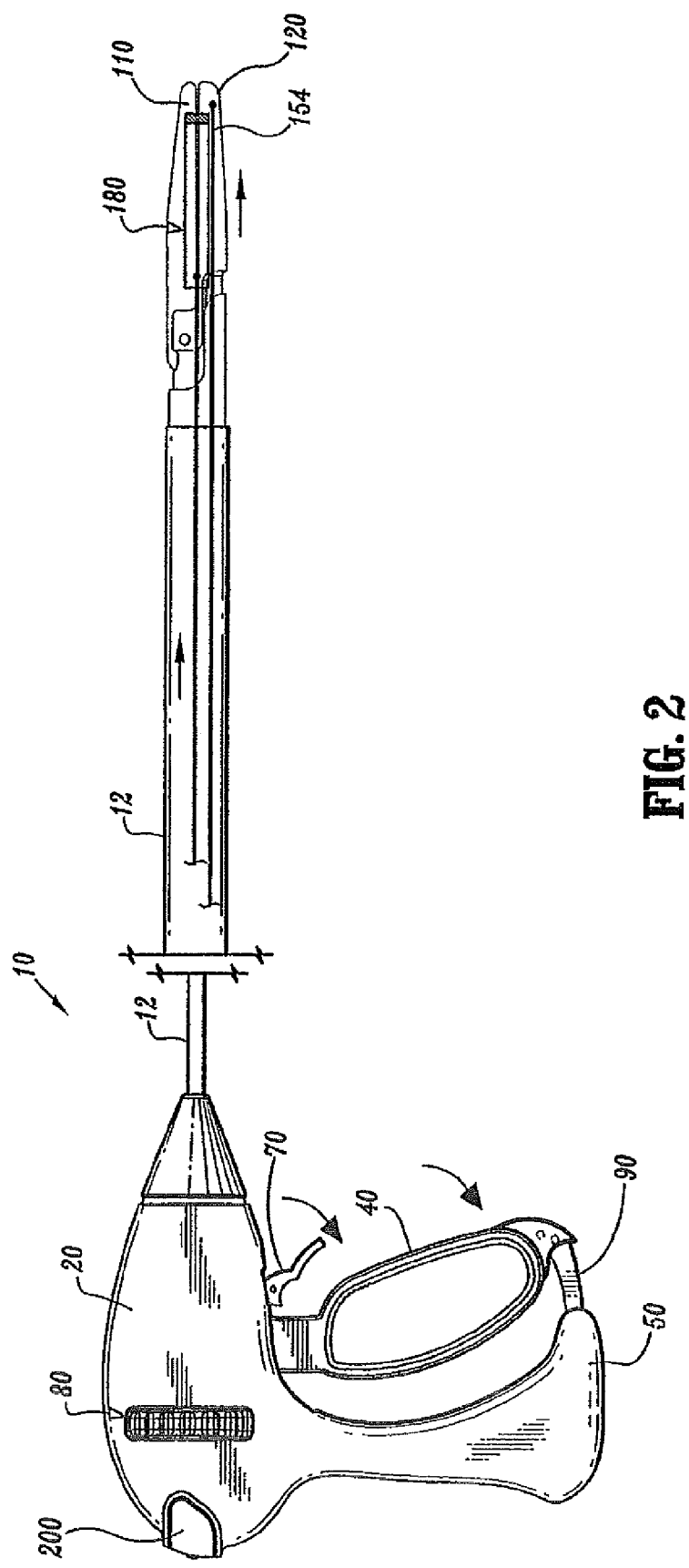
FIG. 2 is a side view of the trigger assembly is a second position for advancing a knife within the end effector assembly.

Turning now to FIGS. 1A-1D, one embodiment of an endoscopic forceps 10 is shown for use with various surgical procedures. For the purposes herein, a vessel sealing forceps is shown and described, however, it is envisioned that other types of forceps or scissors may be utilized which both treat tissue for cauterization, coagulation or other purposes and which may be configured for monopolar applications as described herein. Moreover, although the figure drawings depict a forceps 10 for use in connection with endoscopic surgical procedures, the present disclosure may be used for more traditional open surgical procedures. For the purposes herein, the forceps 10 is described in terms of an endoscopic instrument, however, it is contemplated that an open version of the forceps 10 may also include the same or similar operating components and features as described below.

Forceps 10 generally includes a housing 20, a handle assembly 30, a rotating assembly 80, a trigger assembly 70 and an end effector assembly 100 which mutually cooperate to grasp, treat and divide tissue. For the purposes herein, the handle assembly 30, rotating assembly, trigger assembly 70 and end effector assembly 100 are only generally described. A more detailed explanation of all of these cooperating elements are described in commonly owned, co-pending U.S. patent application Ser. No. 10/460,926 the entire contents of which is hereby incorporated by reference herein.

Forceps 10 includes a shaft 12 which has a distal end 16 dimensioned to mechanically engage the end effector assembly 100 and a proximal end 14 which mechanically engages the housing 20. In the drawings and in the descriptions which follow, the term "proximal", as is traditional, will refer to the end of the forceps 10 which is closer to the user, while the term "distal" will refer to the end which is further from the user. Details of how the shaft 12 connects to the end effector assembly 100 and how the proximal end connects to the housing 20 are explained in the above-mentioned commonly owned, co-pending U.S. patent application Ser. No. 10/460, 926.

As best seen in FIG. 1A, forceps 10 also includes an electrosurgical cable 310 which connects the forceps 10 to a source of electrosurgical energy, e.g., a generator 300. Cable 310 is internally divided into cable leads 310a, 310b and 310c which each transmit electrosurgical energy through their respective feed paths through the forceps 10 to the end effector assembly 100 as explained in more detail with respect to U.S. patent application Ser. No. 10/460,926. Preferably, generators such as those sold by Valleylab—a division of Tyco Healthcare LP, located in Boulder Colo. are used as a source of electrosurgical energy, e.g., FORCE EZ™ Electrosurgical Generator, FORCE FX™ Electrosurgical Generator, FORCE 1C™ Electrosurgical Generator, FORCE 2™ Electrosurgical Generator, SurgiStat™ II Electrosurgical Generator. One such system is described in commonly-owned U.S. Pat. No. 6,033,399 the entire contents of which are hereby incorporated by reference herein. Other systems have been described in commonly-owned U.S. Pat. No. 6,187,003 the entire contents of which is also incorporated by reference herein.

Preferably, the generator 300 includes various safety and performance features including isolated output, independent activation of accessories. Preferably, the electrosurgical generator 300 includes Valleylab's Instant Response™ technology which provides an advanced feedback system to sense changes in tissue 200 times per second and adjust voltage and current to maintain appropriate power.

Handle assembly 30 includes a fixed handle 50 and a movable handle 40. Fixed handle 50 is integrally associated with housing 20 and handle 40 is movable relative to fixed handle 50. Rotating assembly 80 is preferably integrally associated with the housing 20 and is rotatable approximately 180 degrees in either direction about a longitudinal axis "A". Details of the handle assembly 30 and the rotating assembly 80 are described in more detail with respect to U.S. patent application Ser. No. 10/460,926.

As mentioned above, end effector assembly 100 is attached at the distal end 16 of shaft 12 and includes a pair of opposing jaw members 110 and 120. Movable handle 40 of handle assembly 30 is ultimately connected to an internally disposed drive assembly (not shown) which, together, mechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue therebetween.

Turning now to the more detailed features of one embodiment of the present disclosure as described with respect to FIGS. 1A-3, movable handle 40 includes an aperture 42 defined therethrough which enables a user to grasp and move the handle 40 relative to the fixed handle 50. More particularly, handle 40 is selectively moveable about a pivot (not shown) from a first position relative to fixed handle 50 to a second position in closer proximity to the fixed handle 50 which imparts movement of the jaw members 110 and 120 relative to one another.

The lower end of the movable handle 40 includes a flange 90 which, upon movement of the handle 40 proximally, is reciprocated within fixed handle 50. Flange 90 rides within a predefined channel (not shown) disposed within fixed handle 50 to lock the movable handle 40 relative to the fixed handle 50.

As best shown in FIG. 1C, a locking flange 44 is disposed on the outer periphery of the handle 40 above the upper portion of the handle 40. Locking flange 44 prevents the trigger assembly 70 from firing when the handle 40 is oriented in a non-actuated position, i.e., the jaw members 110 and 120 are open. As can be appreciated, this prevents accidental or premature severing of tissue prior to completion of a tissue seal.

As explained in detail in co-pending U.S. patent application Ser. No. 10/460,926, movable handle 40 is designed to provide a distinct mechanical advantage over conventional handle assemblies due to the unique position of the pivot point relative to the longitudinal axis "A" of the shaft 12. In other words, by positioning the pivot point above the driving element, the user gains lever-like mechanical advantage to actuate the jaw members 110 and 120 enabling the user to close the jaw members 110 and 120 with lesser force while still generating the required forces necessary to effect a proper and effective tissue seal. It is also envisioned that the unilateral design of the end effector assembly 100 will also increase mechanical advantage.

As best seen in FIGS. 1A and 1D, the end effector assembly 100 includes opposing jaw members 110 and 120 which cooperate to effectively grasp tissue for sealing purposes. The end effector assembly 100 is designed as a unilateral assembly, i.e., jaw member 120 is fixed relative to the shaft 12 and jaw member 110 pivots about a pivot pin 103 to grasp tissue.

More particularly, the unilateral end effector assembly 100 includes one stationary or fixed jaw member 120 mounted in fixed relation to the shaft 12 and pivoting jaw member 110 mounted about a pivot pin 103 attached to the stationary jaw member 120. A reciprocating sleeve 60 is slidingly disposed within the shaft 12 and is remotely operable by the drive assembly (not shown) which cooperates with handle 40 as explained above to open and close the jaw members 110 and 120. The pivoting jaw member 110 includes a detent or protrusion 117 which extends from jaw member 110 through an aperture 62 disposed within the reciprocating sleeve 60 (FIG. 1D). The pivoting jaw member 110 is actuated by sliding the sleeve 60 axially within the shaft 12 such that aperture 62 abuts against the detent 117 on the pivoting jaw member 110. Pulling the sleeve 60 proximally closes the jaw members 110 and 120 about tissue grasped therebetween and pushing the sleeve 60 distally opens the jaw members 110 and 120 for approximating and grasping purposes.

Once actuated, handle 40 moves in a generally arcuate fashion towards fixed handle 50 about the pivot point which forces the driving flange (not shown) proximally against the drive assembly (not shown) which, in turn, pulls reciprocating sleeve 60 in a generally proximal direction to close jaw member 110 relative to jaw member 120. Moreover, proximal rotation of the handle 40 causes the locking flange 44 to release, i.e., "unlock" the trigger assembly 70 for selective actuation. These features are shown and explained in detail with reference to commonly-owned, co-pending U.S. application Ser. No. 10/460,926.

As best illustrated in FIGS. 5A-5C, a knife channel 115a and 115b runs through the center of the jaw members 110 and 120, respectively, such that a blade 185 can cut tissue grasped between the jaw members 110 and 120 when the jaw members 110 and 120 are in a closed position. More particularly, the blade 185 can only be advanced through the tissue when the jaw members 110 and 120 are closed thus preventing accidental or premature activation of the blade 185 through tissue. Put simply, the knife channel 115 (made up of half channels 115a and 115b) is blocked when the jaws members 110 and 120 are opened and aligned for distal activation when the jaw members 110 and 120 are closed.

As best shown in FIG. 1D, jaw member 110 includes a jaw housing 116 which has an insulative substrate or insulator 114 and an electrically conducive surface 112. Insulator 114 is preferably dimensioned to securely engage the electrically conductive sealing surface 112. This may be accomplished by stamping, by overmolding, by overmolding a stamped electrically conductive sealing plate, by overmolding a metal injection molded seal plate and/or other ways known in the art. It is envisioned a trigger lead 311 from switch 200 electrically connects to the seal plate 112.

All of these manufacturing techniques produce jaw member 110 having an electrically conductive surface 112 which is substantially surrounded by an insulating substrate 114. The insulator 114, electrically conductive sealing surface 112 and the outer, non-conductive jaw housing 116 are preferably dimensioned to limit and/or reduce many of the known undesirable effects related to tissue sealing, e.g., flashover, thermal spread and stray current dissipation.

As best seen in FIG. 10, jaw member 110 also includes a pivot flange 118 which includes protrusion 117. Protrusion 117 extends from pivot flange 118 and includes an arcuately-shaped inner surface dimensioned to matingly engage the aperture 62 of sleeve 60 upon retraction thereof. Pivot flange 118 is also dimensioned to engage pivot pin 103 to allow jaw member 110 to rotate relative to jaw member 120 upon retraction of the reciprocating sleeve 60. Pivot pin 103 also mounts to the stationary jaw member 120 within a proximal portion of jaw member 120.

Preferably, the electrically conductive surface 112 and the insulator 114, when assembled, form the longitudinally-oriented knife slot 115a defined therethrough for reciprocation of the knife blade 185. As mentioned above, knife channel 115a cooperates with corresponding knife channel 115b defined in stationary jaw member 120 to facilitate longitudinal translation of the knife blade 185 along a preferred cutting plane to effectively and accurately separate tissue along the formed tissue seal.

Jaw member 120 includes similar elements to jaw member 110 such as jaw housing 126 having an insulator 124 and an electrically conductive sealing surface 122 which is dimensioned to securely engage the insulator 124. Likewise, the electrically conductive surface 122 and the insulator 124, when assembled, include longitudinally-oriented channel 115b defined therethrough for reciprocation of the knife blade 185. As mentioned above, when the jaw members 110 and 120 are closed about tissue 420, knife channels 115a and 115b form a complete knife channel 115 to allow longitudinal translation of the knife 185 in a distal fashion to sever tissue along the tissue seal.

As mentioned above, jaw member 120 may include a series of stop members 150a-150c preferably disposed on the inner facing surfaces of the electrically conductive sealing surface 122 to facilitate gripping and manipulation of tissue and to define a gap "G". (FIG. 5A) between opposing jaw members 110 and 120 during sealing and cutting of tissue. It is envisioned that the series of stop members 150a-150c may be employed on one or both jaw members 110 and 120 depending upon a particular purpose or to achieve a desired result. A detailed discussion of these and other envisioned stop members 150a-150c as well as various manufacturing and assembling processes for attaching and/or affixing the stop members 150a-150c to the electrically conductive sealing surfaces 112, 122 are described in commonly-assigned, co-pending U.S. Application Ser. No. PCT/US01/11413 which is hereby incorporated by reference in its entirety herein.

Jaw member 120 is designed to be fixed to the end of a rotating tube (not shown) which is part of the rotating assembly 80 such that rotation of the tube will impart rotation to the end effector assembly 100. Jaw member 120 is connected to a second electrical potential through the rotating tube (not shown) which is connected at its proximal end to a lead 310c from cable 310. Details relating to the mechanical and electromechanical engagement of the jaw member 120 to the rotating assembly 80 are described in above-mentioned, commonly-owned, co-pending U.S. patent application Ser. No. 10/460,926.

As mentioned above, the jaw members 110 and 120 may be opened, closed and rotated to manipulate tissue until sealing is desired. This enables the user to position and re-position the forceps 10 prior to activation and sealing. As illustrated in FIG. 1A, the end effector assembly 100 is rotatable about longitudinal axis "A" through rotation of the rotating assembly 80. It is envisioned that the unique feed path of the trigger lead 311 from the switch 200 through the rotating assembly 80, along shaft 12 and, ultimately, to the jaw member 110 enables the user to rotate the end effector assembly 100 about 180 degrees in both the clockwise and counterclockwise direction without tangling or causing undue strain on the cable lead. The other cable lead 310c from cable 310 is fused or clipped to the proximal end of the rotating tube (not shown) and is generally unaffected by rotation of the jaw members 110 and 120. As can be appreciated, this facilitates the grasping and manipulation of tissue.

Again as best shown in FIGS. 1A and 1C, trigger assembly 70 mounts atop movable handle 40 and cooperates with the knife assembly 180 (FIGS. 2, 3, 4, and 5A-5C) to selectively translate knife 185 through a tissue seal. More particularly, the trigger assembly 70 includes a finger actuator 71 and a pivot pin 73 which mounts the trigger assembly 70 to the housing 20. Finger actuator 71 is dimensioned to abut the locking flange 44 on handle 40 when the handle 40 is disposed in a non-actuated position, i.e., the jaw members 110 and 120 are opened.

The trigger assembly 70 is designed to cooperate with a drive bar 64 which connects to the knife assembly 180. Proximal activation of the finger actuator 71 rotates the trigger assembly 70 about pivot pin 73 which, in turn, forces the drive bar 64 distally, which ultimately extends the knife 185 through tissue. A spring (not shown) may be employed to bias the knife assembly 180 in a retracted position such that after severing tissue the knife 185 and the knife assembly 180 are automatically returned to a pre-firing position. In addition, when the handle 40 is actuated and flange 90 is fully reciprocated within fixed handle 50, the locking flange 44 moves proximally allowing activation of the trigger assembly 70.

Figure 3:
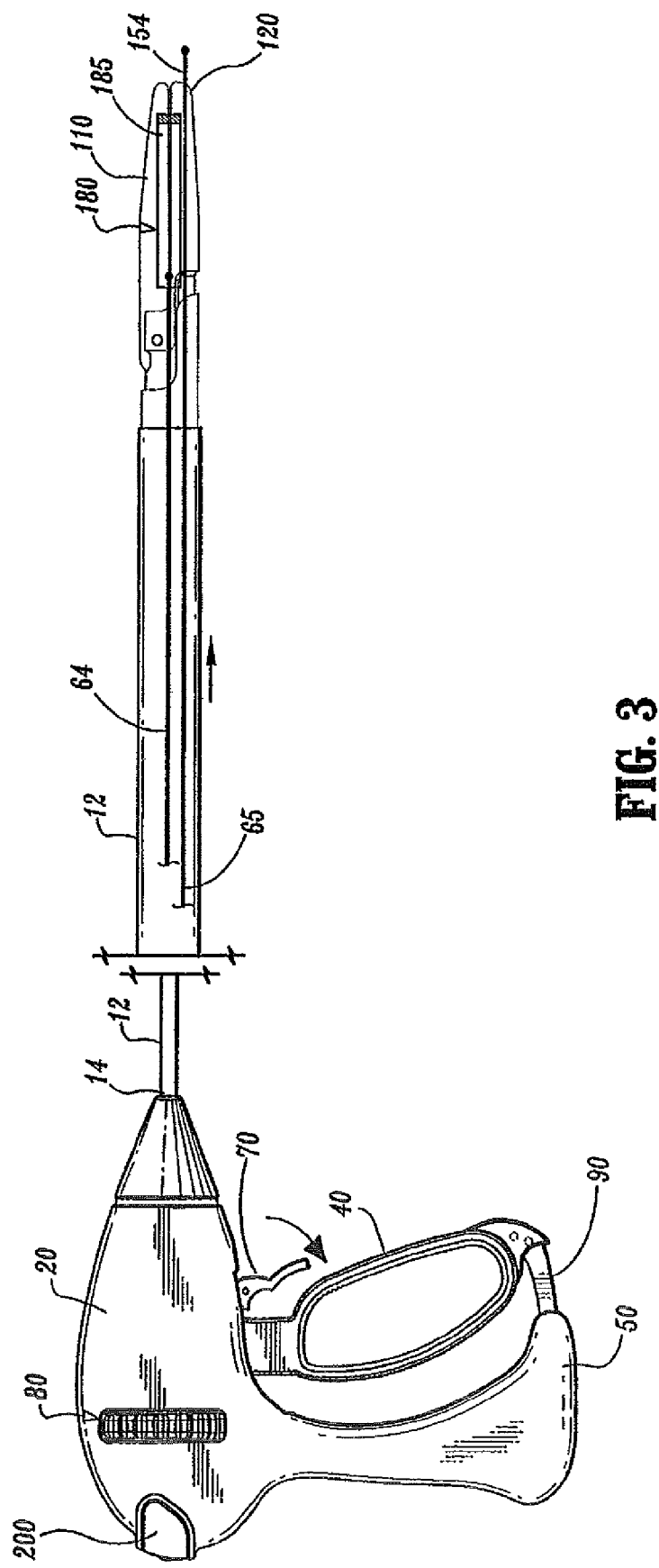
FIG. 3 is a side view of the trigger assembly in a third position for extending a monopolar element from a distal end of the end effector assembly.

Preferably, the monopolar element 154 is connected to a reciprocating rod 65 which extends through an elongated notch 13 in the outer periphery of the shaft 12 as best seen in FIG. 1B. Drive rod 64 which actuates the knife 185 extends through the inner periphery of shaft 12. In order to extend the monopolar element 154, the jaw members 110 and 120 are initially closed and the knife 185 is advanced distally utilizing the trigger assembly 70 (See FIG. 2). As best shown in FIG. 1C, the trigger 71 is initially advanced to translate the knife 185 distally to cut through tissue, i.e., the "cut" stage (shown in phantom). Thereafter and as shown in FIG. 3, the trigger 71 may be further actuated in a proximal direction to extend the monopolar element 154, i.e., the "extend" stage (shown in phantom).

As explained in detail above, the second electrical potential (i.e., lead 310c) is conducted to jaw member 120 through the rotating tube. The two potentials are preferably isolated from one another by insulative sheathing (or the like) which surrounds the trigger lead. Preferably, the jaw members 110 and 120 are electrically isolated from one another such that bipolar electrosurgical energy can be effectively transferred through the tissue to form a tissue seal.

Once the desired position for the sealing site is determined and the jaw members 110 and 120 are properly positioned, handle 40 may be compressed fully such that the flange 90 is reciprocated and locked within fixed handle 50. Handle 40 is now secured in position relative to fixed handle 50 which, in turn, locks the jaw members 110 and 120 in a closed position about tissue. The forceps 10 is now ready for selective application of electrosurgical energy and subsequent separation of tissue, i.e., when movable handle 10 reciprocates within fixed handle 50, locking flange 44 moves into a position to permit activation of the trigger assembly 70 as explained above.

As can be appreciated, the combination of the mechanical advantage of the over-the-center pivot along with the assisting compressive forces associated with a compression spring (not shown) facilitate and assure consistent, uniform and accurate closure pressure about tissue within the desired working pressure range of about 3 kg/cm$^2$ to about 16 kg/cm$^2$ and, preferably about 7 kg/cm$^2$ to about 13 kg/cm$^2$. As mentioned above, at least one jaw member, e.g., 120, may include a stop member e.g., 150a, which limits the movement of the two opposing jaw members 110 and 120 relative to one another. Preferably, a series of stop members are to yield a consistent and accurate gap distance "G" during sealing (FIG. 5A) which ranges from about 0.001 inches to about 0.006 inches and, more preferably, between about 0.002 and about 0.003 inches. By controlling the intensity, frequency and duration of the electrosurgical energy applied to the tissue, the user can effectively seal the tissue along a predetermined tissue site.

As energy is being selectively transferred to the end effector assembly 100, across the jaw members 110 and 120 and through the tissue, a tissue seal forms isolating two tissue halves. At this point and with other known vessel sealing instruments, the user must remove and replace the forceps 10 with a cutting instrument (not shown) to divide the tissue halves along the tissue seal which is both time consuming and tedious and may result in inaccurate tissue division across the tissue seal due to misalignment or misplacement of the cutting instrument along the ideal tissue cutting plane.

The present disclosure incorporates knife assembly 180 which, when activated via the trigger assembly 70, progressively and selectively divides the tissue along an ideal tissue plane in precise manner to effectively and reliably divide the tissue. The knife assembly 180 allows the user to quickly separate the tissue immediately after sealing without substituting a cutting instrument through a cannula or trocar port. As can be appreciated, accurate sealing and dividing of tissue is accomplished with the same forceps 10.

Once the tissue is divided into tissue halves, the jaw members 110 and 120 may be opened by re-grasping the handle 40 which release the flange 90 from fixed handle 50. Details relating to the releasing of the flange from handle are described in commonly-owned, co-pending U.S. application Ser. No. 10/460,926.

Figure 6A:
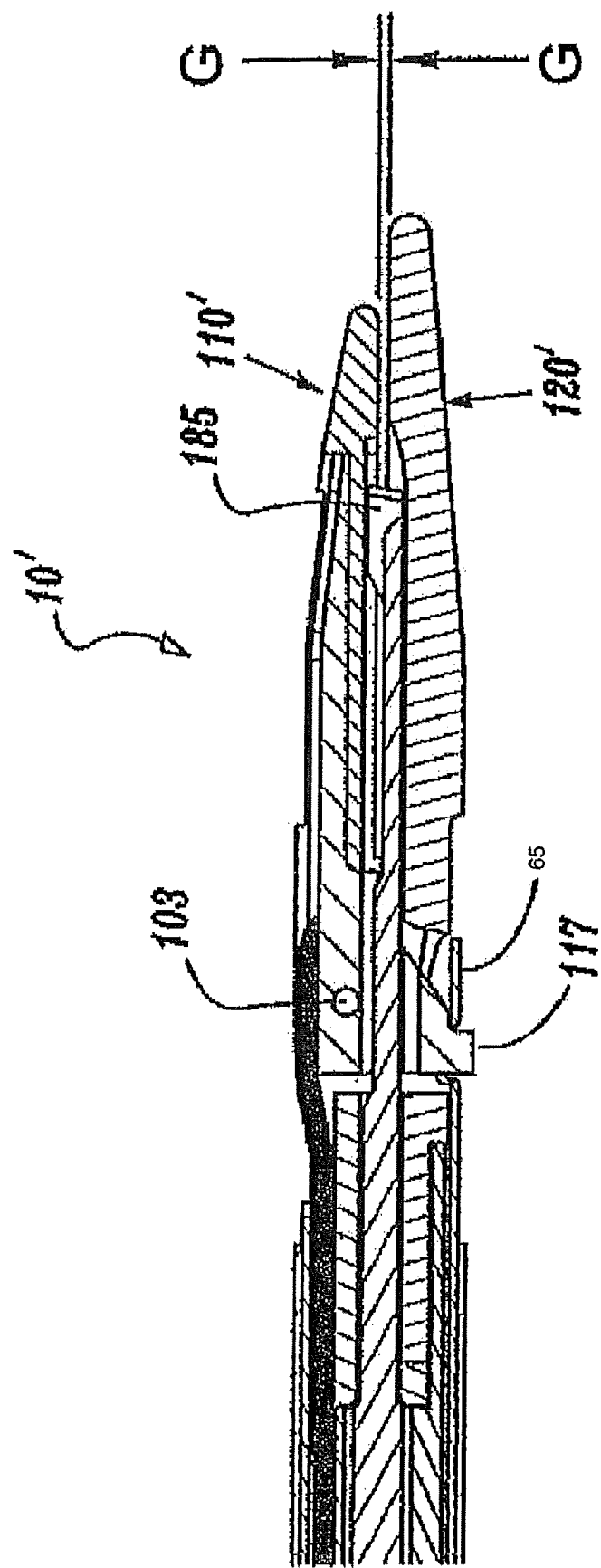
FIG. 6A is an enlarged, side schematic view of another embodiment of an end effector assembly showing a first jaw member extending beyond a second jaw member.

Turning now to the operating characteristics of the present disclosure and as seen in the majority of the figures, forceps 10 is designed for both bipolar electrosurgical treatment of tissue (either by vessel sealing as described above or coagulation or cauterization with other similar instruments) and monopolar treatment of tissue. For example, FIGS. 1A-D and 2-4 show one embodiment of a forceps 10 which includes a monopolar element 154 which may be selectively extended and selectively activated to treat tissue. FIGS. 5A-5C show an alternate embodiment of the present disclosure which shows that the knife 185 may be extended from the distal end of the end effector assembly 100 and selectively energized to treat tissue in a monopolar fashion. FIG. 6A shows another embodiment wherein the bottom jaw member 120' extends distally from the top jaw member 110' to allow the surgeon to selectively energize the bottom jaw member 120' and treat tissue in a monopolar fashion. FIG. 6B shows yet another embodiment wherein the jaw members 110" and 120" include tapered distal ends which are selectively energized with a single electrical potential to treat tissue in a monopolar fashion.

Figure 4:
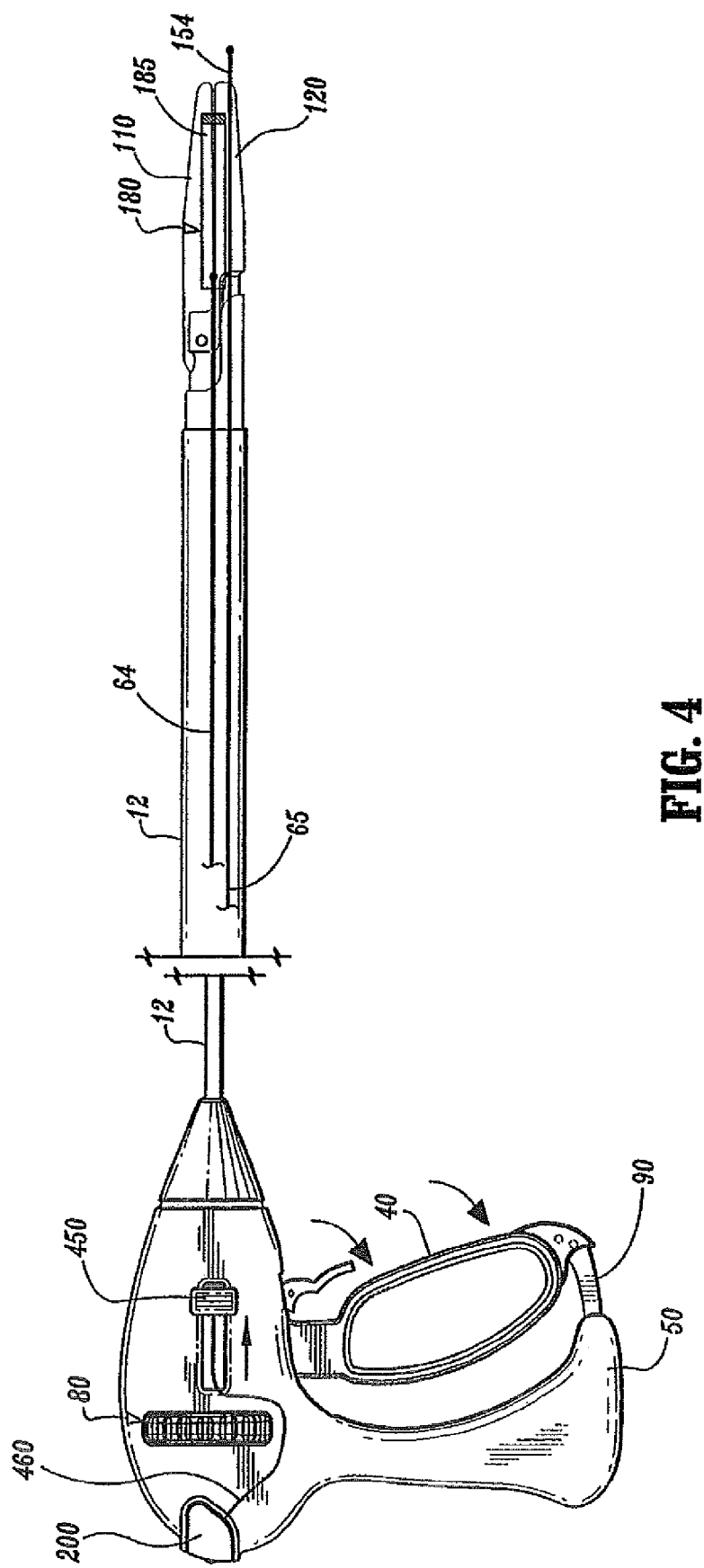
FIG. 4 is a side view of an alternate embodiment of the present invention showing a second actuator advancing the monopolar element relative to the distal end of the end effector assembly.

FIGS. 1A-1D and 2-4 show one embodiment wherein a monopolar element 154 is housed for selective extension within one jaw member, e.g., jaw member 120, of the end effector assembly 100. More particularly, monopolar element 154 is designed to move independently from knife assembly 180 and may be extended by further proximal movement of the trigger assembly 70 (FIGS. 1A, 2 and 3) or by a separate actuator 450 (FIG. 4).

As best shown in FIG. 1A, the cable 310 is fed through the bottom of the housing 20 through fixed handle 50. A first lead 310c extends directly from cable 310 into the rotating assembly 80 and connects (via a fused clip or spring clip or the like) to tube (not shown) to conduct the second electrical potential to fixed jaw member 120. Second and third leads 310a and 310b extend from cable 310 and connect to the hand switch or joy-stick-like toggle switch 200. Switch 200 permits the user to selectively activate the forceps 10 in a variety of different orientations, i.e., multi-oriented activation which simplifies activation. When the switch 200 is depressed, a trigger lead 311 carries the first electrical potential to jaw member 110. More particularly, the trigger lead 311 extends from switch 200 through the rotating assembly 80 and along the upper portion of the rotating tube (not shown) and eventually connects to the movable jaw member 110. As can be appreciated, locating the switch 200 on the forceps 10 has many advantages. For example, the switch 200 reduces the amount of electrical cable in the operating room and eliminates the possibility of activating the wrong instrument during a surgical procedure due to "line-of-sight" activation.

It is envisioned that the trigger assembly 70 may be designed such that the monopolar element 154 may be extended when the jaw members 110 and 120 are in the open position. For example, the trigger 71 may be moved distally (or upwardly) from its original, rested, neutral or pre-actuated position to advance the monopolar element 154. Alternatively, the monopolar element 154 may be advanced irrespective of the orientation of the jaw members 110 and 120. For example, the trigger assembly 70 could be designed such that the it can be moved laterally (i.e., perpendicular to the longitudinal axis "A") to advance the monopolar element 154 or the trigger assembly 70 could be designed such that the monopolar element 154 is extendible when the trigger 71 is moved to a proximal-most position (i.e., past the "cut" position as described above) and/or when the trigger 71 is advanced distally from the neutral or pre-actuated orientation. A return spring (not shown) may be included to return the monopolar element 154 to a non-extended position upon release of the trigger 71.

Upon extension of the monopolar element 154, the generator 300 is preferably configured to automatically switch the forceps 10 from a bipolar activation mode (i.e., deactivating energy delivery to jaw members 110 and 120) to a monopolar activation mode (i.e., activating the monopolar element 154). As can be appreciated, the forceps 10 may also (or alternatively) be configured for manual switching between the bipolar activation mode and the monopolar activation mode.

As described above, when the forceps 10 is configured for bipolar operation, the activation of switch 200 transfers energy from jaw member 110 through the tissue and to jaw member 120 to treat tissue. In the monopolar mode, activation of switch 200 (or a separate switch, e.g., a footswitch), transfers energy to the monopolar element 154, through the tissue and to a return electrode 550, e.g., a return pad, placed adjacent to or in contact with the patient. The monopolar activation mode allows the monopolar element 154 to quickly treat avascular tissue structures and/or quickly dissect narrow tissue planes.

As can be appreciated, it is also envisioned that the trigger assembly 70 may be electrically configured to transmit electrical energy to the monopolar element 154 when extended. For example, the trigger assembly 70 may be configured such that proximal-most actuation of the trigger 71 (FIG. 1C) both extends and activates the monopolar element 154. An automatic safety circuit 460 (or mechanical safety lock (not shown)) may be employed which prevents the switch 200 from energizing the jaw members 110 and 120 when the monopolar element 154 is extended.

FIG. 4 shows another embodiment of the present disclosure wherein the monopolar element 154 is selectively extendible utilizing a second actuator 450. As described above, the knife 185 is advanced by actuating the trigger 71 in a generally proximal direction. The monopolar element 154 is selectively advanceable independently of the knife 185 and may be extended when the jaw members 110 and 120 are disposed in either the open configuration or closed configuration. It is envisioned that the actuator 450 may be electrically configured to activate the monopolar element 154 automatically once extended or manually by activation switch 200 or perhaps another switch (not shown). As mentioned above, a safety circuit 460 may be employed to deactivate jaw members 110 and 120 when the monopolar element 154 is extended such that activation of the switch 200 energizes the monopolar element 154. In the case of a separate activation switch for the monopolar element, the safety circuit would deactivate the switch 200.

FIG. 5A-5C show an alternate embodiment of the present disclosure wherein the knife 185 can be extended distally beyond the jaw members 110 and 120 and separately energized to treat tissue. In this instance, when the knife is extended beyond the jaw members 110 and 120, the knife 185 becomes the monopolar element.

For example and as depicted in the activation sequence shown in FIGS. 5A-5C, the knife 185 is initially seated in a neutral position during tissue approximation and grasping and during the sealing process. Once the jaw members 110 and 120 are closed about tissue, the elongated knife channel 115 (defined by upper and lower knife channels 115a and 115b, respectively) is formed to allow selective translation of the knife 185 through tissue disposed between the jaw members 110 and 120. Upon actuation of the trigger 71, the knife bar 64 forces the knife 185 distally through the tissue to the distal end of the knife channel 115. A stop 119 is included to temporarily limit the movement of the knife 185 and provide the user with positive tactile feedback as to the end of the cutting stroke. Upon further actuation of the trigger 71, the knife 185 overcomes the limiting forces associated with the stop 119 and is forced by the knife bar to further extend out of the knife channel 115 and beyond the distal ends of the jaw members 110 and 120.

It is envisioned that once the knife 185 extends beyond the jaw members 110 and 120, a safety or switch deactivates energizing circuitry to the jaw members 110 and 120 and activates the energizing circuitry to the knife 185 such that activation of the switch 200 energizes the knife 185 and the jaw members remain neutral. For example, the stop 119 may act as a safety switch such that upon being forced by the knife 185 out of or away from the knife channel 115, the stop 119 deactivates circuitry to the jaw members 110 and 120 and activates circuitry to the monopolar knife 185 and the return electrode 550. A separate lead 69 may be used to electrically communicate with the generator 300. As can be appreciated, the knife 185 may now be used in a monopolar fashion to treat tissue.

Upon release of the trigger 71, the knife 185 automatically retracts into the knife channel 115 and back to the pre-actuated position as shown in FIG. 5A. At the same time the stop 119 reverts to its original position to temporarily block the knife channel 115 for subsequent actuation.

FIG. 6A shows another embodiment of a forceps 10' according to the present disclosure wherein the lower jaw member 120' is designed to extend beyond the distal end of jaw member 110'. In order to switch from a bipolar mode of the operation to a monopolar mode, the surgeon activates a switch or control which energizes jaw member 120' to a first potential and activates a return pad 550 to a second potential. Energy is transferred from jaw member 120, through tissue, and to the return pad 550 to treat tissue.

The distal end of jaw member 120' acts as the monopolar element for treating the tissue and may be shaped accordingly to enhance electrosurgical effect.

FIG. 6B shows yet another schematic embodiment of a forceps 10" according to the present disclosure wherein the distal ends of both jaw members 110 and 120 are shaped to treat tissue when disposed in a monopolar mode. More particularly, the distal tips 112a" and 122a" are preferably elongated or tapered to enhance energy delivery when the forceps 10" is disposed in the monopolar mode. When disposed in the bipolar mode, the tapered ends 112a" and 122a" do not effect treating tissue between electrically conductive plates 112" and 122".

A control switch 500 is preferably included which regulates the transition between bipolar mode and monopolar mode. Control switch 500 is connected to generator 300 via cables 360 and 370. A series of leads 510, 520 and 530 are connected to the jaw members 110, 120 and the return electrode 550, respectively. As best shown in the table depicted in FIG. 6C, each lead 510, 520, and 530 is provided with an electrical potential or remains neutral depending upon the particular "mode" of the forceps 10". For example, in the bipolar mode, lead 510 (and, in turn, jaw member 110") is energized with a first electrical potential and lead 520 (and, in turn, jaw member 120") is energized with second electrical potential. As a result thereof, electrosurgical energy is transferred from jaw member 110" through the tissue and to jaw member 120". The return electrode 550 remains off or neutral.

In a monopolar mode, jaw member 110" and 120" are both energized with the same electrical potential and the return pad 550 is energized with a second electrical potential forcing the electrical current to travel from the jaw members 110" and 120", through the tissue and to the return electrode 550. This enables the jaw members 110" and 120" to treat tissue in a monopolar fashion which, as mentioned above, advantageously treats avascular tissue structures and/or allows quick dissection of narrow tissue planes. As can be appreciated, all of the leads 510, 520 and 530 may be deactivated when the forceps 10" is turned off or idle.

Although the general operating components and inter-cooperating relationships among these components have been generally described with respect to a vessel sealing forceps 10, other instruments may also be utilized which can be configured to allow a surgeon to selectively treat tissue in both a bipolar and monopolar fashion. For example, bipolar grasping and coagulating instruments, cauterizing instruments, bipolar scissors, etc.

The present disclosure also relates to a method for treating tissue with electrosurgical energy from the electrosurgical generator 300 which includes the steps of: providing an endoscopic forceps 10 including a housing 20 having a shaft 12 affixed thereto. The shaft 12 includes first and second jaw members, 110 and 120, respectively, attached to a distal end of the shaft 12. An actuator or handle assembly 30 is included for moving jaw members 110 and 120 relative to one another from a first position wherein the jaw members 110 and 120 are disposed in spaced relation relative to one another to a second position wherein the jaw members 110 and 120 cooperate to grasp tissue therebetween. A monopolar element 154 is also included which is housed within at least the first jaw member 120 and selectively movable from a first position within the first jaw member 120 to a second position distal to the first jaw member 120. A return electrode 550 is provided and placed in contact with patient tissue.

The method also includes the steps of: connecting to each jaw member 110 and 120, the monopolar element 154 and the return electrode 550 to the electrosurgical generator 300; grasping tissue between the jaw members 110 and 120; selectively activating the jaw members 110 and 120 to treat tissue disposed between the jaw members 110 and 120 in a bipolar fashion; and selectively activating the monopolar element 154 and the return electrode 550 independent of the jaw members 110 and 120 to treat tissue in a monopolar fashion.

Preferably, after the step of selectively activating the jaw members 110 and 120 to treat tissue, the method includes the step of: extending the monopolar element 154 from the distal end of the jaw members 110 and 120. Advantageously, the step of selectively activating the monopolar element 154 includes deactivating the jaw members 110 and 120.

After the step of selectively activating the jaw members 110 and 120 to treat tissue, the method may include the step of: releasing the tissue from the jaw members 110 and 120.

From the foregoing and with reference to the various figure drawings, those skilled in the art will appreciate that certain modifications can also be made to the present disclosure without departing from the scope of the same. For example, it may be preferable to add other features to the forceps 10, e.g., an articulating assembly to axially displace the end effector assembly 100 relative to the elongated shaft 12.

It is envisioned that the forceps 10 may be designed such that it is fully or partially disposable depending upon a particular purpose or to achieve a particular result. For example, end effector assembly 100 may be selectively and releasably engageable with the distal end 16 of the shaft 12 and/or the proximal end 14 of shaft 12 may be selectively and releasably engageable with the housing 20 and the handle assembly 30. In either of these two instances, the forceps 10 would be considered "partially disposable" or "reposable", i.e., a new or different end effector assembly 100 (or end effector assembly 100 and shaft 12) selectively replaces the old end effector assembly 100 as needed. As can be appreciated, the presently disclosed electrical connections would have to be altered to modify the instrument to a reposable forceps.

Moreover, it is envisioned that the switch 200 may be decommissioned during the cutting process. Decommissioning the switch 200 when the trigger 71 is actuated eliminates unintentionally activating the forceps during the cutting process. It is also envisioned that the switch 200 may be disposed on another part of the forceps 10, e.g., the fixed handle 40, rotating assembly 80, housing 20, etc.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. An endoscopic forceps, comprising:
 a housing having a shaft affixed thereto, the shaft including first and second jaw members attached to a distal end thereof, each jaw member adapted to connect to a source of electro surgical energy such that the jaw members are selectively capable of conducting energy through tissue held therebetween to treat tissue;
 an actuator operably associated with the housing for moving the jaw members relative to one another from a first position wherein the jaw members are disposed in spaced relation relative to one another to a second position wherein the jaw members cooperate to grasp tissue therebetween;
 a knife that is selectively moveable within a knife channel defined within at least one of the first and second jaw members to cut tissue disposed between the first and second jaw members;
 a monopolar element housed within at least the first jaw member and selectively movable from a first position within the first jaw member to a second position distal to the first jaw member, the monopolar element adapted to connect to a source of electrosurgical energy and selectively activateable independent of the jaw members; and
 a trigger configured to move proximally to a first position to move the knife to divide tissue disposed between the jaw members and to move further proximally to a second position to extend the monopolar element from the first position within the first jaw member to the second position distal to the first jaw member, wherein the trigger is configured to selectively move the monopolar element from the first position to the second position when the jaw members are in the first position and wherein the trigger is configured to move to a third position proximal to the second position to selectively cause the source of electrosurgical energy to supply energy to the monopolar element.

2. An endoscopic forceps according to claim 1 wherein the forceps is a vessel sealing forceps and at least one of the jaw members includes at least one non-conductive stop member disposed thereon configured to control the distance between the first and second jaw members when tissue is held therebetween.

3. An endoscopic forceps according to claim 1, wherein the trigger is configured to selectively cause a source of electrosurgical energy to supply energy to the monopolar element.

4. An endoscopic forceps according to claim 1, wherein the monopolar element is configured to return to the first position upon movement of the trigger distally from the second position.

5. An endoscopic forceps according to claim 1, wherein upon movement of the monopolar element to the second position, a supply of electrosurgical energy to the jaw members is deactivated and the supply of electrosurgical energy to the monopolar element is activated.

6. A system for an electrosurgical forceps, comprising:
 an instrument housing having a shaft affixed thereto, the shaft including first and second jaw members attached to a distal end thereof;
 an actuator operably associated with the housing for moving the jaw members relative to one another from a first position wherein the jaw members are disposed in spaced relation relative to one another to a second position wherein the jaw members cooperate to grasp tissue therebetween;
 an energy source adapted to provide energy to each jaw member such that the jaw members are configured to conduct bipolar energy through tissue grasped therebetween;
 a knife that is selectively moveable within a knife channel defined within at least one of the first and second jaw members to cut tissue grasped between the first and second jaw members;
 a monopolar element housed within at least the first jaw member and selectively movable from a first position within the first jaw member to a second position distal to the first jaw member, the monopolar element connected to the energy source and selectively activateable independent of the jaw members; and
 a trigger moveable from a neutral position to a first position to move the knife to divide tissue grasped between the jaw members and from the first position to a second position proximal to the first position to extend the monopolar element from the first position within the first jaw member to the second position distal to the first jaw member, wherein the trigger is configured to move to a third position proximal to the second position to selectively cause the energy source to supply energy to the monopolar element.

\* \* \* \* \*